(12) United States Patent
Comper et al.

(10) Patent No.: US 11,407,991 B2
(45) Date of Patent: Aug. 9, 2022

(54) NUCLEIC ACID EXTRACTION FROM HETEROGENEOUS BIOLOGICAL MATERIALS

(71) Applicant: Exosome Diagnostics, Inc., Cambridge, MA (US)

(72) Inventors: Wayne Comper, New York, NY (US); Leileata M. Russo, New York, NY (US); Johan Karl Olov Skog, New York, NY (US)

(73) Assignee: Exosome Diagnostics, Inc., Waltham, MA (US)

( * ) Notice: Subject to any disclaimer, the term of this patent is extended or adjusted under 35 U.S.C. 154(b) by 0 days.

(21) Appl. No.: 15/138,746

(22) Filed: Apr. 26, 2016

(65) Prior Publication Data

US 2016/0237422 A1    Aug. 18, 2016

Related U.S. Application Data

(63) Continuation of application No. 14/116,372, filed as application No. PCT/US2012/037443 on May 11, 2012, now abandoned.

(60) Provisional application No. 61/485,112, filed on May 11, 2011.

(51) Int. Cl.
| | | |
|---|---|---|
| *C07H 21/00* | (2006.01) | |
| *C12N 15/10* | (2006.01) | |
| *C07H 21/02* | (2006.01) | |
| *C07H 1/08* | (2006.01) | |
| *C12Q 1/6806* | (2018.01) | |
| *C12Q 1/68* | (2018.01) | |
| *G01N 33/00* | (2006.01) | |

(52) U.S. Cl.
CPC ........... *C12N 15/1003* (2013.01); *C07H 1/08* (2013.01); *C07H 21/02* (2013.01); *C12N 15/101* (2013.01); *C12N 15/1006* (2013.01); *C12Q 1/6806* (2013.01)

(58) Field of Classification Search
CPC ....... C12Q 1/68; C07H 21/00; C12N 15/1003
See application file for complete search history.

(56) References Cited

U.S. PATENT DOCUMENTS

| | | | | |
|---|---|---|---|---|
| 4,767,710 A | * | 8/1988 | Bigbee | .................... C07K 16/34 435/343 |
| 5,219,727 A | | 6/1993 | Wang et al. | |
| 5,538,871 A | | 7/1996 | Nuovo et al. | |
| 5,556,773 A | | 9/1996 | Yourno | |
| 5,582,981 A | | 12/1996 | Toole et al. | |
| 5,639,606 A | | 6/1997 | Willey | |
| 5,639,611 A | | 6/1997 | Wallace et al. | |
| 5,766,840 A | * | 6/1998 | Kim | .................... C07K 14/005 435/5 |
| 5,840,867 A | | 11/1998 | Toole et al. | |
| 6,004,755 A | | 12/1999 | Wang | |
| 6,180,778 B1 | * | 1/2001 | Bastian | .............. C12N 15/1006 536/25.3 |
| 6,525,154 B1 | | 2/2003 | Shea et al. | |
| 6,812,023 B1 | | 11/2004 | Lamparski et al. | |
| 6,893,837 B2 | | 5/2005 | Slamon et al. | |
| 6,899,863 B1 | | 5/2005 | Dhellin et al. | |
| 6,913,879 B1 | | 7/2005 | Schena | |
| 6,994,960 B1 | | 2/2006 | Foote et al. | |
| 7,074,563 B2 | | 7/2006 | Köster | |
| 7,186,512 B2 | | 3/2007 | Martienssen et al. | |
| 7,198,893 B1 | | 4/2007 | Köster et al. | |
| 7,198,923 B1 | | 4/2007 | Abrignani et al. | |
| 7,332,553 B2 | | 2/2008 | Sellergren et al. | |
| 7,364,848 B2 | | 4/2008 | Van Beuningen et al. | |
| 7,378,245 B2 | | 5/2008 | Liu | |
| 7,384,589 B2 | | 6/2008 | Hart et al. | |
| 9,707,333 B2 | * | 7/2017 | Ichim | .................... A61M 1/362 |
| 2003/0199078 A1 | * | 10/2003 | Kleiber | .................... B03C 1/01 435/270 |
| 2004/0121411 A1 | | 6/2004 | Roberts et al. | |
| 2004/0204661 A1 | * | 10/2004 | Epler | .................... B01L 3/5055 600/572 |
| 2005/0063961 A1 | * | 3/2005 | Friedlander et al. ......................... C12N 5/0647 424/93.21 |
| 2006/0211032 A1 | * | 9/2006 | Huang | ............... C12N 15/1003 435/6.1 |

(Continued)

FOREIGN PATENT DOCUMENTS

| | | |
|---|---|---|
| WO | WO 01/36601 A | 5/2001 |
| WO | WO 2003/023065 A1 | 3/2003 |

(Continued)

OTHER PUBLICATIONS

Ahern, H. The Scientist 9(15) : 20 (Year: 1995).*

(Continued)

*Primary Examiner* — Bradley L. Sisson

(74) *Attorney, Agent, or Firm* — Cooley LLP; Ivor R. Elrifi; Matthew Pavao

(57) ABSTRACT

Methods for extracting high quality nucleic acids from a heterogenous collection of nucleic acid-containing materials from a biological sample are disclosed. The heterogenous collection of nucleic-acid containing materials may contain cells or microvesicles, or both. The extractions obtained by the methods described herein are characterized by high yield and high integrity, making the extracted nucleic acids useful for various applications in which high quality nucleic acid extractions are preferred, e.g., a diagnosis, prognosis, or therapy evaluation for a medical condition.

15 Claims, 3 Drawing Sheets

(56) References Cited

U.S. PATENT DOCUMENTS

| | | | |
|---|---|---|---|
| 2007/0254351 A1 | 11/2007 | Abrignani et al. | |
| 2008/0268429 A1* | 10/2008 | Pietrzkowski | A61K 47/6901 435/6.18 |
| 2009/0311270 A1* | 12/2009 | Allen | C12N 15/1034 514/1.1 |
| 2009/0311715 A1* | 12/2009 | Owen | G01N 33/6893 435/7.1 |
| 2010/0184046 A1* | 7/2010 | Klass | C12Q 1/6886 435/7.1 |
| 2010/0196426 A1* | 8/2010 | Skog | C12Q 1/6806 424/400 |
| 2010/0316688 A1* | 12/2010 | Bamdad | C12N 5/0647 424/423 |
| 2011/0003704 A1* | 1/2011 | Skog | C12Q 1/6806 506/9 |
| 2011/0053157 A1* | 3/2011 | Skog | C12Q 1/6806 435/6.18 |
| 2011/0089315 A1* | 4/2011 | Walt | G02B 17/0615 250/251 |
| 2011/0195426 A1* | 8/2011 | Russo | C12N 15/1017 435/6.17 |
| 2012/0142001 A1* | 6/2012 | Skog | C07H 1/08 435/6.12 |
| 2012/0238467 A1* | 9/2012 | Taylor | G07F 17/3211 506/9 |
| 2013/0029339 A1* | 1/2013 | Skog | C12Q 1/6858 435/6.12 |
| 2013/0040833 A1* | 2/2013 | Noerholm | C12Q 1/6806 506/9 |
| 2013/0131194 A1* | 5/2013 | Skog | C12Q 1/6806 514/789 |
| 2013/0202559 A1* | 8/2013 | Skog | A61K 9/5184 424/93.2 |
| 2013/0295574 A1* | 11/2013 | Skog | C12N 15/1003 435/6.12 |
| 2014/0045915 A1* | 2/2014 | Skog | C12Q 1/6806 514/44 A |
| 2014/0147839 A1* | 5/2014 | Chen | C12Q 1/6883 435/6.11 |
| 2014/0162888 A1 | 6/2014 | Kuslich et al. | |
| 2014/0194319 A1* | 7/2014 | Skog | C12Q 1/6806 506/9 |
| 2014/0194613 A1* | 7/2014 | Skog | C12Q 1/6806 536/25.41 |
| 2014/0212871 A1* | 7/2014 | Comper | C07H 21/02 435/6.11 |
| 2015/0038335 A1* | 2/2015 | Skog | C12Q 1/6806 506/2 |
| 2015/0176073 A1* | 6/2015 | Skog | C12Q 1/6806 506/2 |
| 2015/0252428 A1* | 9/2015 | Comper | C12Q 1/6886 506/2 |
| 2015/0322532 A1* | 11/2015 | Skog | C12Q 1/6858 424/133.1 |
| 2015/0353920 A1* | 12/2015 | Enderle | C12N 15/1006 536/25.41 |
| 2016/0002736 A1* | 1/2016 | Noerholm | C12Q 1/6809 506/9 |
| 2016/0024491 A1* | 1/2016 | Skog | C12N 15/1003 506/9 |
| 2016/0075788 A1* | 3/2016 | Skog | C12Q 1/6886 424/1.49 |
| 2016/0153053 A1* | 6/2016 | Skog | C12Q 1/6806 506/9 |
| 2016/0161502 A1 | 6/2016 | Duffin et al. | |
| 2016/0177401 A1* | 6/2016 | Skog | C12Q 1/6886 506/9 |
| 2016/0201121 A1* | 7/2016 | Chen | C12Q 1/6883 506/9 |
| 2016/0216253 A1 | 7/2016 | Balaj et al. | |
| 2016/0348095 A1* | 12/2016 | Russo | C12N 15/1017 |
| 2016/0362678 A1* | 12/2016 | Skog | C12Q 1/6806 |
| 2017/0088898 A1* | 3/2017 | Skog | C12Q 1/6883 |
| 2017/0114389 A1* | 4/2017 | Russo | C12Q 1/6806 |
| 2017/0198280 A1* | 7/2017 | Skog | C12N 15/1006 |
| 2017/0314075 A1* | 11/2017 | Skog | C12Q 1/6883 |
| 2018/0340945 A1 | 11/2018 | Mitsuhashi | |
| 2020/0292561 A1 | 9/2020 | Sher et al. | |

FOREIGN PATENT DOCUMENTS

| | | | | |
|---|---|---|---|---|
| WO | WO 2003/050290 A2 | | 6/2003 | |
| WO | WO-2005083081 A1 | * | 9/2005 | G01N 33/573 |
| WO | WO 2006/113590 A2 | | 10/2006 | |
| WO | WO 2007/127848 A | | 11/2007 | |
| WO | WO 2009/100029 | * | 8/2009 | |
| WO | WO-2009100029 A1 | * | 8/2009 | A61P 35/00 |
| WO | WO 2010/065765 A2 | | 6/2010 | |
| WO | WO 2011/009104 | * | 1/2011 | |
| WO | WO 2012/155014 A1 | | 5/2012 | |
| WO | WO 2017/053516 A1 | | 3/2017 | |
| WO | WO 2017/074658 A1 | | 5/2017 | |

OTHER PUBLICATIONS

Baj-Krzyworzeka et al. Cancer Immunol. Immunither 55 : 808 (Year: 2006).*
Chen et al. Nucleic Acids Research 33(20) : e179 (Year: 2005).*
Ciafre et al. BBRC 334:1351 (Year: 2005).*
Clayton et al. J. of Immunological Methods 247 :163 (Year: 2001).*
Heimberger et al. J. of Translational Medicine 3 :38 (Year: 2005).*
Nilsson et al., British . J. of Cancer 100:1603 (Year: 2009).*
Rabinowits et al. Clinical Lung Cancer 10(1) : 42 (Year: 2009).*
Skog et al. Nature Cell Biololgy 10(12) : 1470 (Year: 2008).*
SUPERase-IN Thermoscientific (Year: 2018).*
Taylor et al. Br. J. of Cancer 92:305 (Year: 2005).*
Taylor et al. Gnecologic Oncology 110 : 13 (2008) (Year: 2008).*
Thery et al., Nature Reviews 2 :569 (Year: 2002).*
Thery et al. Current Protocols in Cell Biology 3.22.1 (Year: 2006).*
Vlassov et al. Biochimica et Biophysica Acta 1820: 940 (Year: 2012).*
Zhou et al. Kidney Int. 69(8) : 1471 (Year: 2006).*
Baeuerle et al., EpCAM (CD326) finding its role in cancer. British J. of Cancer 96 : 417 (Year: 2007).*
Balamurugan et al., Surface immobilization methods for aptamer diagnostic applications . Anal. Bioanal. Chem. 390 :1009 (Year: 2008).*
Board et al., Platelet-derived growth factor receptor (PDGFR): A target for anticancer therapeutics. Drug Resistane Updates 8 :75 (Year: 2005).*
Crisan et al.,A Perivascular Origin for Mesenchymal Stem Cells in Multiple Human Organs. Cell Stem Cell 3:301 (Year: 2008).*
Lee et al., Tight-Binding Inhibition of Angiogenin and Ribonuclease A by Placental Ribonuclease Inhibitor. Biochemistry 28 :225 (Year: 1989).*
Nogues et al., BBA 1253 : 16-24 (Year: 1995).*
Michie et al., Nature 360 : 264 (Year: 1992).*
Abravaya, et al., "Detection of point mutations with a modified ligase chain reaction (Gap-LCR)." Nucleic Acids Research (1995); 23 (4): 675-682.
Agarwal, et al., "Immunostaining as an adjunct to cytology for diagnosis of pancreatic adenocarcinoma." Clin Gastroenterol Hepatol. (2008); 6 (12): 1425-1431.
Agis, et al. "Enumeration and immunohistochemical characterisation of bone marrow basophils in myeloproliferative disorders using the basophil specific monoclonal antibody 2D7." Journal of Clinical Pathology (2006); 59 (4): 396-402.
Agis, et al. "Identification of basogranulin (BB1) as a novel immunohistochemical marker of basophils in normal bone marrow and patients with myeloproliferative disorders." Am J Clin Pathol. (2006); 125 (2): 273-281.
Agre, et al., "Biochemistry of the erythrocyte Rh polypeptides: A review." Yale J Biol Med. (1990); 63: 461-4677.
Al-Hajj, et al., "Prospective identification of tumorigenic breast cancer cells." PNAS (2003); 100 (7): 3983-3988.

(56) References Cited

OTHER PUBLICATIONS

Allard, et al,. "Tumor cells circulate in the peripheral blood of all major carcinomas but not in healthy subjects or patients with nonmalignant diseases." Clin Cancer Res. (2004); 10:6897-6904.
Al-Nedawi, et al., "Intercellular transfer of the oncogenic receptor EGFRvIII by microvesicles derived from tumour cells." Nat Cell Biol. (2008); 10 (5): 619-624.
Alsayed, et al., "Mechanisms of regulation of CXCR4/SDF-1 (CXCL12)-dependent migration and homing in multiple myeloma." Blood (2007); 109 (7): 2708-2717.
Alvero, et al., "Molecular phenotyping of human ovarian cancer stem cells unravels the mechanisms for repair and chemoresistance." Cell Cycle (2009); 8 (1): 158-166.
Ammons, et al., "In vitro and in vivo pharmacology and pharmacokinetics of a human engineered monoclonal antibody to epithelial cell adhesion molecule." Neoplasia (2003); 5 (2): 146-154.
Andersson, et al., "Glycophorin A as a cell surface marker of early erythroid differentiation in acute leukemia." Int J Cancer (1979); 24 (6): 717-720.
Avent, et al., "Immunochemical analysis of the human erythrocyte Rh polypeptides." J Biol Chem. (1996); 271 (24): 14233-14239.
Baig, et al., "Hepatocellular carcinoma (HCC) and diagnostic significance of A-fetoprotein (AFP)." J Ayub Med Coll Abbottabad (2009); 21 (1): 72-75.
Ball, et al., "Introduction: workshop summary of the CD15 monoclonal antibody panel from the Fifth International Workshop on Leukocyte Antigens." Eur J Morphol. (1995); 33 (2): 95-100.
Balzar, et al., "The biology of the 17-1A antigen (Ep-CAM)." J Mol Med. (1999); 77 (10): 699-712.
Bao, et al., "Stem cell-like glioma cells promote tumor angiogenesis through vascular endothelial growth factor." Cancer Res. (2006); 66 (16): 7843-7848.
Bao, et al., "Glioma stem cells promote radioresistance by preferential activation of the DNA damage response." Nature (2006); 444 (7120): 756-760.
Bao, et al., "Targeting cancer stem cells through L1CAM suppresses glioma growth." Cancer Res. (2008); 68 (15): 6043-6048.
Bembridge, et al., "Comparison of monoclonal antibodies with potential specificity for restricted isoforms of the leukocyte common antigen (CD45R)." Vet Immunol Immunopathol. (1993); 39(1-3): 129-136.
Berrington, et al., "Lymphocyte subsets in term and significantly preterm UK infants in the first year of life analysed by single platform flow cytometry." Clin Exp Immunol. (2005); 140 (2): 289-292.
Boman, et al., "Human colon cancer stem cells: a new paradigm in gastrointestinal oncology." J Clin Oncol. (2008); 26(17): 2828-2838.
Bonnet, et al., "Human acute myeloid leukemia is organized as a hierarchy that originates from a primitive hematopoietic cell." Nat Med. (1997); 3(7): 730-737.
Borgono, et al,. "Human kallikrein 14: a new potential biomarker for ovarian and breast cancer." Cancer Res. (2003); 63 (24): 9032-9041.
Borregaard, "Biosynthesis of granule proteins in normal human bone marrow cells. Gelatinase is a marker of terminal neutrophil differentiation." Blood (1995); 85 (3): 812-817.
Bossi, et al., "Molecularly imprinted polymers for the recognition of proteins: the state of the art." Biosens Bioelectron. (2007); 22 (6): 1131-1137.
Chan, et al., "Identification, molecular characterization, clinical prognosis, and therapeutic targeting of human bladder tumor-initiating cells." PNAS (2009); 106 (33): 14016-14021.
Chang, et al., "Five Different Anti-Prostate-specific Membrane Antigen (PSMA) Antibodies Confirm PSMA Expression in Tumor-associated Neovasculature." Cancer Res. (1999); 59 (13): 3192-3198.
Chang, et al., "Molecular cloning of mesothelin, a differentiation antigen present on mesothelium, mesotheliomas, and ovarian cancers." PNAS (1996); 93(1): 136-140.

Chen, et al., Apolipoprotein Eis required for cell proliferation and survival in ovarian cancer. Cancer Res. (2005); 65: 331-337.
Chen, et al., "Microfluidic isolation and transcriptome analysis of serum microvesicles." Lab Chip (2010); 10 (4): 505-511.
Cheruvanky, et al., "Rapid isolation of urinary exosomal biomarkers using a nanomembrane ultrafiltration concentrator." Am J Physiol Renal Physiol. (2007); 292: F1657-F1661.
Clement, et al., "Analysis of the monocyte Fc receptors and antibody-mediated cellular interactions required for the induction of T cell proliferation by anti-T3 antibodies." J Immunol. (1985); 135 (1): 165-171.
Coiffier, "Rituximab therapy in malignant lymphoma." Oncogene (2007); 26 (25): 3603-3613.
Collins, et al.,"Prospective identification of tumorigenic prostate cancer stem cells." Cancer Res. (2005); 65 (23):10946-10951.
Coren, et al., "CD45 immunoaffinity depletion of vesicles from Jurkat T cells demonstrates that exosomes contain CD45: no evidence for a distinct exosome/HIV-1 budding pathway." Retrovirology (2008); 5: 64, pp. 1-5.
Cotton, et al., "Reactivity of cytosine and thymine in single-base-pair mismatches with hydroxylamine and osmium tetroxide and its application to the study of mutations." Proc Natl Acad Sci U S A (1988); 85 (12): 4397-4401.
Cowell and Lo, "Application of oligonucleotides arrays for coincident comparative genomic hybridization, ploidy status and loss of heterozygosity studies in human cancers." Methods Mol Biol. (2009); 556: 47-65.
Cox, et al., "Characterization of acute lymphoblastic leukemia progenitor cells." Blood (2004); 104 (9): 2919-2925.
Dallas, et al., "Chemoresistant colorectal cancer cells, the cancer stem cell phenotype, and increased sensitivity to insulin-like growth factor-I receptor inhibition." Cancer Res. (2009); 69 (5):1951-1957.
De Clerck, et al. "Expression of neutrophil activation markers and neutrophil adhesion to chondrocytes in rheumatoid arthritis patients: relationship with disease activity." Res Immunol. (1995); 146 (2): 81-87.
De La Fuente, et al., "Molecular characterization and expression of a novel human leukocyte cell-surface marker homologous to mouse Ly-9." Blood (2001); 97 (11): 3513-3520.
Dhanasekaran, et al. "Delineation of prognostic biomarkers in prostate cancer." Nature (2001);412(6849): 822-826.
Ding, et al., "Expression and purification of recombinant cytoplasmic domain of human erythrocyte band 3 with hexahistidine tag or chitin-binding tag in *Escherichia coli*." Protein Expr Purif. (2004); 34 (2): 167-175.
Dirks, P.B., "Glioma migration: clues from the biology of neural progenitor cells and embryonic CNS cell migration." J Neurooncol. (2001); 53 (2): 203-212.
Ducrest, et al., "Flowcytometric analysis of basophil counts in human blood and inaccuracy of hematology analyzers." Allergy (2005); 60 (11): 1446-1450.
Eramo, et al., "Identification and expansion of the tumorigenic lung cancer stem cell population." Cell Death Differ. (2008); 15 (3): 504-514. Epub Nov. 30, 2007.
Extended European Search Report for European Application No. EP 12782575.0, dated Nov. 4, 2014, 8 pages.
Falleni, et al., "Survivin gene expression in early-stage non-small cell lung cancer." J Pathol. (2003); 200 (5): 620-626.
Fayle, et al., "Isolation of plasma membrane from human blood monocytes. Subcellular fractionation and marker distribution." Eur J Biochem. (1985); 147 (2): 409-419.
Ferrandina, et al., "Expression of CD133-1 and CD133-2 in ovarian cancer." Int J Gynecol Cancer (2008); 18 (3): 506-514. Epub Sep. 13, 2007.
Figarella-Branger, et al., "Differential spectrum of expression of neural cell adhesion molecule isoforms and L1 adhesion molecules on human neuroectodermal tumors." Cancer Res. (1990); 50 (19): 6364-6370.
Fillmore and Kuperwasser, "Human breast cancer cell lines contain stem-like cells that self-renew, give rise to phenotypically diverse progeny and survive chemotherapy." Breast Cancer Res. (2008); 10(2): R25.

(56) References Cited

OTHER PUBLICATIONS

Fink, et al., "Monocyte activation markers during cardiopulmonary bypass." Perfusion (2003); 18 (2): 83-86.
Fischer and Lerman, "[11] Two-dimensional electrophoretic separation of restriction enzyme fragments of DNA." Methods in Enzymology (1979); 68: 183-191.
Fischer and Lerman, "Length-independent separation of DNA restriction fragments in two-dimensional gel electrophoresis." Cell (1979); 16 (1): 191-200.
Flaherty, et al., "CD11/CD18 leukocyte integrins: new signaling receptors for bacterial endotoxin." J Surg Res. (1997); 73 (1): 85-89 . . . .
Flanagan, et al., "Localization of the Epstein-Barr virus protein LMP 1 to exosomes." J Gen Virol. (2003); 84(Pt 7): 1871-1879.
Fong and Kakar, "The role of cancer stem cells and the side population in epithelial ovarian cancer." Histol Histopathol. (2010); 25 (1): 113-120.
Galli, et al., "Isolation and characterization of tumorigenic, stem-like neural precursors from human glioblastoma." Cancer Res. (2004); 64 (19): 7011-7021.
Gallin, et al., A neutrophil membrane marker reveals two groups of chronic myelogenous leukemia and its absence may be a marker of disease progression. Blood (1986); 68 (2): 343-346.
Geiss, et al., "Direct multiplexed measurement of gene expression with color-coded probe pairs." Nat Biotechnol. (2008); 26 (3): 317-325.
Ginestier, et al., "ALDH1 is a marker of normal and malignant human mammary stem cells and a predictor of poor clinical outcome." Cell Stem Cell. (2007); (5): 555-567.
Goel, et al., "Pharmacokinetic and safety study of subcutaneously administered weekly ING-1, a human engineere monoclonal antibody targeting human EpCAM, in patients with advanced solid tumors." Ann Oncol. (2007); 18 (10): 1704-1707.
Guatelli, et al., "Isothermal, in vitro amplification of nucleic acids by a multienzyme reaction modeled after retroviral replication." Proc Natl Acad Sci U S A. (1990); 87 (5): 1874-1878.
Guerini, et al., "Human leukocyte antigen distribution analysis in North Italian brain Glioma patients: an association with HLA-DRB1*14." J Neurooncol. (2006); 77 (2): 213-217. Epub Nov. 29, 2005.
Gürlek, et al., What are the markers of aggressiveness in prolactinomas? Changes in cell biology, extracellular matrix components, angiogenesis and genetics. Eur J Endocrinol. (2007); 156 (2): 143-153.
Hahn, "Molecular Biology of Double-Minute Chromosomes." Bioessays (1993); 15 (7): 477-484.
Hannigan, et al., "Leukocyte-specific gene 1 protein (LSP1) is involved in chemokine KC-activated cytoskeletal reorganization in murine neutrophils in vitro." J Leukoc Biol. (2001); 69 (3): 497-504.
Hasenberg, et al., "Rapid immunomagnetic negative enrichment of neutrophil granulocytes from murine bone marrow for functional studies in vitro and in vivo." PLoS One (2011); 6 (2): e17314.
Hemmati, et al., "Cancerous stem cells can arise from pediatric brain tumors." Proc Natl Acad Sci U S A. (2003); 100 (25): 15178-15183.
Hermann, et al., "Distinct populations of cancer stem cells determine tumor growth and metastatic activity in human pancreatic cancer." Cell Stem Cell. (2007); 1 (3): 313-323.
Hessels, et al., "Detection of TMPRSS2-ERG fusion transcripts and prostate cancer antigen 3 in urinary sediments may improve diagnosis of prostate cancer." Clin Cancer Res. (2007); 13 (17): 5103-5108.
Hill, et al., "Genetic markers in glioblastoma: prognostic significance and future therapeutic implications." Adv Anat Pathol. (2003); 10 (4): 212-217.
Hoffman, et al., "Immunofluorometric quantitation and histochemical localisation of kallikrein 6." Br J Cancer (2002); 87 (7): 763-771.
Hosen, et al., "CD96 is a leukemic stem cell-specific marker in human acute myeloid leukemia." Proc Natl Acad Sci U S A. (2007); 104 (26): 11008-11013.
Hough, et al., "Coordinately up-regulated genes in ovarian cancer." Cancer Res. (2001); 61 (10): 3869-3876.
Hurt, et al., "$CD44^+CD24^-$ prostate cells are early cancer progenitor/stem cells that provide a model for patients with poor prognosis." Br J Cancer (2008); 98 (4): 756-765.
Ignatova, et al., "Human cortical glial tumors contain neural stem-like cells expressing astroglial and neuronal markers in vitro." GLIA (2002); 39 (3):193-206.
International Preliminary Report on Patentability for International Application No. PCT/US2012/037443, dated Nov. 21, 2013, 8 pages.
International Search Report and Written Opinion for International Application No. PCT/US2012/037443, dated Jul. 6, 2012, 9 pages.
Ishikawa, et al., "Chemotherapy-resistant human AML stem cells home to and engraft within the bone-marrow endosteal region." Nat Biotechnol. (2007); 25(11): 1315-1321.
Jackman, et al., "Impact of epidermal growth factor receptor and KRAS mutations on clinical outcomes in previously untreated non-small cell lung cancer patients: results of an online tumor registry of clinical trials." Clin Cancer Res. (2009); 15 (16): 5267-5273.
Jiang, et al., "Aldehyde dehydrogenase 1 is a tumor stem cell-associated marker in lung cancer." Mol Cancer Res. (2009); 7 (3): 330-338.
Jiang, et al., "High Dose Chemotherapy and Transplantation of Hematopoietic Progenitors from Murine D3 Embryonic Stem Cells." Journal of Chemotherapy (2005); 17 (3): 302-308.
Jin, et al., "Expression of neural cell adhesion molecule in normal and neoplastic human neuroendocrine tissues." Am J Pathol. (1991); 138 (4): 961-969.
Jin, et al., "Targeting of CD44 eradicates human acute myeloid leukemic stem cells." Nat Med. (2006); 12 (10): 1167-1174.
Johnson, et al., "Surface-immobilized peptide aptamers as probe molecules for protein detection." Anal Chem. (2008); 80 (4): 978-983.
Jonas, et al., "Electron microscopic study of receptor mediated endocytosis of a monoclonal antibody (RoMo-1) against the surface marker CD 14 of human monocytes." Acta Histochem Suppl. (1990); 39: 339-344.
Kalli, et al., "Folate receptor alpha as a tumor target in epithelial ovarian cancer." Gynecol Oncol. (2008); 108(3): 619-626.
Kan and Dozy, "Antenatal diagnosis of sickle-cell anaemia by DNA analysis of amniotic-fluid cells." The Lancet (1978); 312 (8096): 910-912.
Kan and Dozy, "Polymorphism of DNA sequence adjacent to human ß-globin structural gene: relationship to sickle mutation." PNAS (1978); 75(11): 5631-5635.
Kansas, et al., "Molecular mapping of functional domains of the leukocyte receptor for endothelium, LAM-1." J Cell Biol. (1991); 114(2): 351-358.
Kasinrerk, et al., "Human leukocyte activation antigen M6, a member of the Ig superfamily, is the species homologue of rat OX-47, mouse basigin, and chicken HT7 molecule." J Immunol. (1992); 149 (3): 847-854.
Kawanishi, et al., "Secreted CXCL1 Is a Potential Mediator and Marker of the Tumor Invasion of Bladder Cancer." Clin Cancer Res (2008); 14 (9): 2579-2587.
Keller, et al., "CD24 is a marker of exosomes secreted into urine and amniotic fluid." Kidney Int. (2007); 72 (9): 1095-1102.
Kepley, et al., "Identification and partial characterization of a unique marker for human basophils." J Immunol (1995); 154 (12): 6548-6555.
Kim, et al., "The multidrug resistance transporter ABCG2 (breast cancer resistance protein 1) effluxes Hoechst 33342 and is overexpressed in hematopoietic stem cells." Clin Cancer Res. (2002); 8(1): 22-28.
Kobayashi, et al., "Expression of organic cation transporter OCTN1 in hematopoietic cells during erythroid differentiation." Exp Hematol. (2004); 32 (12):1156-1162.

(56) References Cited

OTHER PUBLICATIONS

Kojima and Kitamura, "A signal sequence trap based on a constitutively active cytokine receptor." Nat Biotechnol. (1999); 17 (5): 487-490.
Komminoth, et al., "Polysialic acid of the neural cell adhesion molecule distinguishes small cell lung carcinoma from carcinoids." Am J Pathol. (1991); 139 (2): 297-304.
Korkaya, et al., "HER2 regulates the mammary stem/progenitor cell population driving tumorigenesis and invasion." Oncogene (2008); 27 (47): 6120-6130.
Kwoh, et al., "Transcription-based amplification system and detection of amplified human immunodeficiency virus type 1 with a bead-based sandwich hybridization format." Proc Natl Acad Sci U S A (1989); 86: 1173-1177.
Lai, et al., "Tissue distribution of restricted leukocyte common antigens. A comprehensive study with protein- and carbohydrate-specific CD45R antibodies." Lab Invest. (1991); 64 (6): 844-854.
Landegren, et al., "A ligase-mediated gene detection technique." Science (1988); 241 (4869): 1077-1080.
Lapidot, et al., "A cell initiating human acute myeloid leukaemia after transplantation into SCID mice." Nature (1994); 367 (6464): 645-648.
Laxman et al., "A first-generation multiplex biomarker analysis of urine for the early detection of prostate cancer." Cancer Research (2008); 68: 645-649.
Lee, et al., "Tumor stem cells derived from glioblastomas cultured in bFGF and EGF more closely mirror the phenotype and genotype of primary tumors than do serum-cultured cell lines." Cancer Cell. (2006); 9 (5): 391-403.
Lewis, et al., "An erythrocyte-specific protein that binds to the poly(dG) region of the chicken ß-globin gene promoter." Genes & Dev. (1988); 2: 863-873.
Li, et al., "Evidence for mesenchymal-epithelial transition associated with mouse hepatic stem cell differentiation." PLoS One (2011); 6(2): e17092.
Li, et al., "Identification of pancreatic cancer stem cells." Cancer Res. (2007); 67 (3): 1030-1037.
Li, et al., "Replacing PCR with COLD-PCR enriches variant DNA sequences and redefines the sensitivity of genetic testing." Nature Medicine (2008); 14 (5): 579-584.
Lim and Oh, "The role of CD24 in various human epithelial neoplasias." Pathol Res Pract. (2005); 201 (7): 479-486.
Liu, et al., "Analysis of gene expression and chemoresistance of CD133+ cancer stem cells in glioblastoma." Mol Cancer (2006); 5: 67.
Lu, et al., "Selection of potential markers for epithelial ovarian cancer with gene expression arrays and recursive descent partition analysis." Clin Cancer Res. (2004); 10 (10): 3291-3300.
Lunter, et al., "Activated leukocyte cell adhesion molecule (ALCAM/CD166/MEMD), a novel actor in invasive growth, controls matrix metalloproteinase activity." Cancer Res. (2005); 65 (19): 8801-8808.
Luo, et al., "Prognostic value of human kallikrein 10 expression in epithelial ovarian carcinoma." Clin Cancer Res. (2001); 7 (8): 2372-2379.
Maglara, et al., "The combination of human glandular kallikrein and free prostate-specific antigen (PSA) enhances discrimination between prostate cancer and benign prostatic hyperplasia in patients with moderately increased total PSA." Clin Chem. (1999); 45 (11): 1960-1966.
Magro, et al., "Proteomic and postproteomic characterization of keratan sulfate-glycanated isoforms of thyroglobulin and transferrin uniquely elaborated by papillary thyroid carcinomas." Am J Pathol. (2003); 163 (1): 183-196.
Marafioti, et al., "Leukocyte-specific phosphoprotein-1 and PU.1: two useful markers for distinguishing T-cell-rich B-cell lymphoma from lymphocyte-predominant Hodgkin's disease." Haematologica (2004); 89 (8): 957-964.
Masuoka, et al., "Monoclonal antibodies to feline lymphocyte membranes recognize the leukocyte-common antigen (CD45R)." J Vet Med Sci. (1992); 54: 865-870.
Matsui, et al., "CD64 on neutrophils is a sensitive and specific marker for detection of infection in patients with rheumatoid arthritis." J Rheumatol. (2006); 33 (12): 2416-2424.
Matsui, et al., "Characterization of clonogenic multiple myeloma cells." Blood (2004); 103 (6): 2332-2336. Epub Nov. 20, 2003.
Matthews, et al., "Epithelial cell markers and proliferating cells in odontogenic jaw cysts." J Pathol. (1988); 156 (4): 283-290.
Mattick, J.S., "RNA regulation: a new genetics?" Nat Rev Genet. (2004); 5 (4): 316-323.
McGuckin, et al., "Prognostic significance of MUC1 epithelial mucin expression in breast cancer." Hum Pathol. (1995); 26 (4): 432-439.
Miele, et al., "Autocatalytic replication of a recombinant RNA." J Mol Biol. (1983); 171: 281-295.
Min-Oo, et al., "Phenotypic expression of pyruvate kinase deficiency and protection against malaria in a mouse model." Genes Immun. (2004); 5 (3): 168-175.
Miranda, et al., "Nucleic acids within urinary exosomes/microvesicles are potential biomarkers for renal disease." Kidney International (2010); 78 (2): 191-199.
Monzani, et al., "Melanoma contains CD133 and ABCG2 positive cells with enhanced tumourigenic potential." Eur J Cancer (2007); 43 (5): 935-946.
Myers, et al., "Detection of single base substitutions by ribonuclease cleavage at mismatches in RNA:DNA duplexes." Science (1985); 230 (4731): 1242-1246.
Nakazawa, et al., "UV and skin cancer: specific p53 gene mutation in normal skin as a biologically relevant exposure measurement." Proc Natl Acad Sci U S A. (1994); 91: 360-364.
Naundorf, et al., "In vitro and in vivo activity of MT201, a fully human monoclonal antibody for pancarcinoma treatment." Int J Cancer (2002); 100 (1):101-110.
Neve, et al., "A collection of breast cancer cell lines for the study of functionally distinct cancer subtypes." Cancer Cell (2006); 10 (6): 515-527.
Nishitani, et al., "Fibroblast-specific protein 1 is a specific prognostic marker for renal survival in patients with IgAN." Kidney Int. (2005); 68 (3): 1078-1085.
Niv, Y., "MUC1 and colorectal cancer pathophysiology considerations." World J Gastroenterol. (2008); 14 (14): 2139-2141.
Oberneder, et al., "A phase I study with adecatumumab, a human antibody directed against epithelial cell adhesion molecule, in hormone refractory prostate cancer patients." Eur J Cancer (2006); 42 (15): 2530-2538.
O'Brien, et al., "A human colon cancer cell capable of initiating tumour growth in immunodeficient mice." Nature (2007); 445 (7123): 106-110.
Oldenborg, et al., "Role of CD47 as a marker of self on red blood cells." Science (2000); 288 (5473): 2051-2054.
Orita, et al., "Detection of polymorphisms of human DNA by gel electrophoresis as single-strand conformation polymorphisms." PNAS (1989); 86 (8): 2766-2770.
Orozco and Lewis, "Flow cytometric analysis of circulating microparticles in plasma." Cytometry A (2010); 77A(6): 502-514.
Ottaiano, et al., "Inhibitory effects of anti-CXCR4 antibodies on human colon cancer cells." Cancer Immunol Immunother. (2005); 54 (8): 781-791. Epub Dec. 11, 2004.
Partin, et al., "Use of human glandular kallikrein 2 for the detection of prostate cancer: preliminary analysis." Urology (1999); 54 (5): 839-845.
Pelloski, et al., "Epidermal Growth Factor Receptor Variant III Status Defines Clinically Distinct Subtypes of Glioblastoma." Journal of Clinical Oncology (2007); 25 (16): 2288-2294.
Prince, et al., "Identification of a subpopulation of cells with cancer stem cell properties in head and neck squamous cell carcinoma." Proc Natl Acad Sci U S A. (2007); 104 (3): 973-978.
Prinetti, et al., "GM3 synthase overexpression results in reduced cell motility and in caveolin-1 upregulation in human ovarian carcinoma cells." Glycobiology (2010); 20 (1): 62-77. doi: 10.1093/glycob/cwp143. Epub Sep. 16, 2009.

(56) References Cited

OTHER PUBLICATIONS

Punnoose, et al., "Molecular Biomarker Analyses Using Circulating Tumor Cells." PLoS One (2010); 5 (9): e12517.
Rangel, et al., "Tight junction proteins claudin-3 and claudin-4 are frequently overexpressed in ovarian cancer but not in ovarian cystadenomas." Clin Cancer Res. (2003); 9 (7): 2567-2575.
Raposo, et al., "B lymphocytes secrete antigen-presenting vesicles." Journal of Experimental Medicine (1996); 183: 1161-1172.
Ricci-Vitiani, et al., "Identification and expansion of human colon-cancer-initiating cells." Nature (2007); 445 (7123):111-115. Epub Nov. 19, 2006.
Rittenhouse, et al., "Human Kallikrein 2 (hK2) and prostate-specific antigen (PSA): two closely related, but distinct, kallikreins in the prostate." Crit Rev Clin Lab Sci. (1998); 35 (4): 275-368.
Rosen, et al., "Potential markers that complement expression of CA125 in epithelial ovarian cancer." Gynecol Oncol. (2005); 99 (2): 267-277.
Ross, et al., "Correlation of primary tumor prostate-specific membrane antigen expression with disease recurrence in prostate cancer." Clin Cancer Res. (2003); 9 (17): 6357-6362.
Rudolph, et al., "Immunophenotyping of dermal spindle cell tumors: diagnostic value of monocyte marker Ki-M1p and histogenetic considerations." Am J Surg Pathol. (1997); 21 (7): 791-800.
Ruppert, et al., "IL-4 decreases the expression of the monocyte differentiation marker CD14, paralleled by an increasing accessory potency." Immunobiology (1991); 182 (5): 449-464.
Sagiv, et al., "CD24 is a new oncogene, early at the multistep process of colorectal cancer carcinogenesis." Gastroenterology (2006); 131 (2): 630-639.
Sainte-Laudy and Belon, "Improvement of flow cytometric analysis of basophil activation inhibition by high histamine dilutions. A novel basophil specific marker: CD 203c." Homeopathy (2006); 95 (1): 3-8.
Salmaggi, et al., "Glioblastoma-derived tumorospheres identify a population of tumor stem-like cells with angiogenic potential and enhanced multidrug resistance phenotype." GLIA (2006); 54 (8): 850-860.
Santin, et al., "Trastuzumab treatment in patients with advanced or recurrent endometrial carcinoma overexpressing HER2/neu." Int J Gynaecol Obstet. (2008); 102 (2): 128-131.
Schatton, et al., "Identification of cells initiating human melanomas." Nature (2008); 451 (7176): 345-349.
Shan, et al., "Five monoclonal antibodies against glycophorin A of human erythrocyte recognize glycoprotein of bovine erythrocyte." Hybridoma (1998); 17 (1): 55-62.
Shangguan, et al., "Cell-specific aptamer probes for membrane protein elucidation in cancer cells." J Proteome Res. (2008); 7 (5): 2133-2139.
Sheu and Shih, "Clinical and biological significance of HLA-G expression in ovarian cancer." Semin Cancer Biol. (2007); 17 (6):436-443.
Shih and Davidson, "Pathogenesis of ovarian cancer: clues from selected overexpressed genes." Future Oncol. (2009); 5 (10):1641-1657.
Shmelkov, et al., "CD133 expression is not restricted to stem cells, and both CD133+ and CD133− metastatic colon cancer cells initiate tumors." J Clin Invest. (2008); 118 (6): 2111-2120.
Siegel, et al., "Induction of mesenchymal/epithelial marker expression in human amniotic fluid stem cells." Reprod Biomed Online (2009); 19 (6): 838-846.
Singh, et al., "Identification of a cancer stem cell in human brain tumors." Cancer Res. (2003); 63 (18): 5821-5828.
Singh, et al., "Identification of human brain tumour initiating cells." Nature (2004); 432 (7015): 396-401.
Smith, et al., "CD133/prominin-1 is a potential therapeutic target for antibody-drug conjugates in hepatocellular and gastric cancers." Br J Cancer (2008); 99 (1):100-109.
Spiekermann, et al., "Identification of the antigen recognized by the monoclonal antibody 31D8." Exp Hematol. (1996); 24 (3):453-458.
Steemers, et al., "Whole-genome genotyping with the single-base extension assay." Nature Methods (2006); 3: 31-33.
Stott, et al., "Isolation of circulating tumor cells using a microvortex-generating herringbone-chip." Proc Natl Acad Sci U S A. (2010); 107 (43): 18392-18397.
Strojnik, et al., "Neural stem cell markers, nestin and musashi proteins, in the progression of human glioma: correlation of nestin with prognosis of patient survival." Surg Neurol. (2007); 68 (2): 133-143.
Strutz, et al., "Identification and characterization of a fibroblast marker: FSP1." J Cell Biol. (1995); 130 (2): 393-405.
Sun, et al., "Skeletal Localization and Neutralization of the SDF-1(CXCL12)/CXCR4 Axis Blocks Prostate Cancer Metastasis and Growth in Osseous Sites In Vivo." J Bone Miner Res. (2005); 20 (2): 318-329. Epub Nov. 16, 2004.
Tao, et al., "The application of CD71 and Hoechst33258 to staining method for sorting fetal nucleated red blood cells in the peripheral blood of pregnant women." Zhonghua Yi Xue Yi Chuan Xue Za Zhi. (2000); 17 (5): 352-354 (with English Abstract).
Taylor, et al., "Radial glia cells are candidate stem cells of ependymoma." Cancer Cell (2005); 8 (4): 323-335.
Taylor-Papadimitriou, et al., "MUC1 and cancer." Biochim Biophys Acta (1999); 1455 (2-3): 301-313.
Telen and Chasis, "Relationship of the human erythrocyte Wrb antigen to an interaction between glycophorin A and band 3." Blood (1990); 76 (4): 842-848.
Thibert, et al., "Increased platelet CD36 constitutes a common marker in myeloproliferative disorders." Br J Haematol. (1995); 91 (3): 618-624.
Thomas, et al., "Identification, characterization and utilization of tumor cell selectin ligands in the design of colon cancer diagnostics." Biorheology (2009); 46 (3): 207-225.
Ting, et al., "Aberrant Overexpression of Satellite Repeats in Pancreatic and Other Epithelial Cancers." Science (2011); 331 (6017): 593-596.
Todaro, et al., "Colon cancer stem cells dictate tumor growth and resist cell death by production of interleukin-4." Cell Stem Cell (2007); 1 (4): 389-402.
Tu, et al., "A functional role for circulating mouse L-selectin in regulating leukocyte/endothelial cell interactions in vivo." J Immunol. (2002); 169 (4): 2034-2043.
Uchida, et al., "Direct isolation of human central nervous system stem cells." Proc Natl Acad Sci U S A. (2000); 97 (26): 14720-14725.
Valent, et al., "Further characterization of surface membrane structures expressed on human basophils and mast cells." Int Arch Allergy Appl Immunol. (1990); 91 (2): 198-203.
Van Der Vos, et al., "Brain Tumor Microvesicles: Insights into Intercellular Communication in the Nervous System." Cellular and Molecular Neurobiology (2011); 31 (6): 949-959.
Velculescu, et al., "Serial Analysis of Gene Expression." Science (1995); 270 (5235): 484-487.
Venturi, et al., "Leukocyte migration is regulated by L-selectin endoproteolytic release." Immunity (2003); 19 (5): 713-724.
Visintin, et al., "Diagnostic markers for early detection of ovarian cancer." Clin Cancer Res. (2008); 14 (4): 1065-1072.
Walker, et al., "Growth factor receptor expression in anal squamous lesions: modifications associated with oncogenic human papillomavirus and human immunodeficiency virus." Hum Pathol. (2009); 40(11): 1517-1527.
Went, et al., "Frequent EpCam protein expression in human carcinomas." Hum Pathol. (2004); 35: 122-128.
Yang and Chang, "Bladder Cancer Initiating Cells (BCICs) Are Among EMA-CD44v6+ Subset: Novel Methods for Isolating Undetermined Cancer Stem (Initiating) Cells." Cancer Investigation (2008); 26 (7): 725-733.
Yang, et al., "Significance of CD90+ cancer stem cells in human liver cancer." Cancer Cell (2008); 13 (2): 153-166.
Yin and Lloyd, "Molecular cloning of the CA125 ovarian cancer antigen: identification as a new mucin, MUC16." J Biol Chem. (2001); 276 (29): 27371-27375.
Yin, et al., "Ovarian cancer antigen CA125 is encoded by the MUC16 mucin gene." Int J Cancer (2002); 98 (5): 737-740.

(56) References Cited

OTHER PUBLICATIONS

Yokohama, et al., "Acute basophilic leukemia lacking basophil-specific antigens: the importance of cytokine receptor expression in differential diagnosis." Int J Hematol. (2002); 75 (3): 309-313.

Yousef, et al., "Human kallikrein 5: a potential novel serum biomarker for breast and ovarian cancer." Cancer Res. (2003); 63 (14): 3958-3965.

Yousef, et al., "Parallel overexpression of seven kallikrein genes in ovarian cancer." Cancer Res. (2003); 63 (9): 2223-2227.

Yuan, et al., "Isolation of cancer stem cells from adult glioblastoma multiforme." Oncogene (2004); 23 (58): 9392-9400.

Zeppernick, et al., "Stem cell marker CD133 affects clinical outcome in glioma patients." Clin Cancer Res. (2008); 14(1): 123-129.

Zhong, et al., "Expression of CD147 is associated with prostate cancer progression." International Journal of Cancer (2012); 130 (2): 300-308.

Zwicker, et al., "Tumor-derived tissue factor-bearing microparticles are associated with venous thromboembolic events in malignancy." Clin Cancer Res. (2009); 15 (22): 6830-6840.

Koliha, et al., "A novel multiplex bead-based platform highlights the diversity of extracellular vesicles," Journal of Extracellular Vesicles (2016); 5: 29975, 15 pages; http://dx.doi.org/10.3402/jev.v5.29975.

Ko, J. et al., "Smartphone-enabled optofluidic exosome diagnostic for concussion recovery," Scientific Reports, 6:31215 (2016), 12 pages; doi:10.1038/srep31215.

Oksvold, M. P. et al., "Chapter 27: Magnetic Bead-Based Isolation of Exosomes," Methods in Molecular Biology, 1218:465-481 (2015).

Zarovni, N. et al., "Integrated isolation and quantitative analysis of exosome shuttled proteins and nucleic acids using immunocapture approaches," Methods, 87:46-58 (2015).

Zocco, D. & Zarovni, N., "Chapter 22: Extraction and Analysis of Extracellular Vesicle-Associated miRNAs Following Antibody-Based Extracellular Vesicle Capture from Plasma Samples," Plant Genotyping, Extracellular Vesicles: Methods and Protocols, Methods in Molecular Biology, 1660:269-285 (2017); doi: 10.1007/978-1-4939-7253-1_22.

GRIA2, Wikipedia; retrieved from the Internet on Dec. 18, 2021, 11 pages.

\* cited by examiner

NUCLEIC ACID EXTRACTION FROM HETEROGENEOUS BIOLOGICAL MATERIALS

RELATED APPLICATIONS

This application is a continuation application which claims benefit to U.S. national stage application Ser. No. 14/116,372, filed on Nov. 8, 2013 under 35 U.S.C. § 371, of PCT Application No. PCT/US2012/037443, filed May 11, 2012, which claims benefit to U.S. Provisional Application No. 61/485,112, filed May 11, 2011, the contents of each of which are hereby incorporated by reference in their entirety.

FIELD OF INVENTION

The present invention relates to the general field of nucleic acid analysis, particularly the procurement and analysis of high quality nucleic acids from a sample of heterogeneous biological materials.

BACKGROUND

Increasing knowledge of the genetic and epigenetic changes occurring in cancer cells provides an opportunity to detect, characterize, and monitor tumors by analyzing tumor-related nucleic acid sequences and profiles. Cancer-related biomarkers include, e.g., specific mutations in gene sequences (Cortez and Calin, 2009; Diehl et al., 2008; Network, 2008; Parsons et al., 2008), up- and down-regulation of mRNA and miRNA expression (Cortez and Calin, 2009; Itadani et al., 2008; Novakova et al., 2009), mRNA splicing variations, changes in DNA methylation patterns (Cadieux et al., 2006; Kristensen and Hansen, 2009), amplification and deletion of genomic regions (Cowell and Lo, 2009), and aberrant expression of repeated DNA sequences (Ting et al., 2011). Various molecular diagnostic assays such as mutational analysis, methylation status of genomic DNA, and gene expression analysis may detect these biomarkers and provide valuable information for doctors, clinicians and researchers. These tests so far utilize cancer cells derived from surgically removed tumor tissue or from tissue obtained by biopsy.

However, the ability to perform these tests using a bodily fluid is oftentimes more desirable than using a patient tissue sample. A less invasive approach using a bodily fluid sample has wide ranging implications in terms of patient welfare, the ability to conduct longitudinal disease monitoring, and the ability to obtain expression profiles even when tissue cells are not easily accessible, e.g., in ovarian or brain cancer patients.

The present invention is directed to methods and systems for extracting high quality nucleic acid from a biological sample, preferably a fluid sample, and the resulting nucleic acid extractions. The subject methods, systems and extractions may be used in support of patient diagnostics, prognostics, theranostics, monitoring, predictive medicine, personalized medicine, integrated medicine, pharmacodiagnostics and diagnostic/prescription partnering (companion diagnostics).

SUMMARY

In general terms, the present invention is a new method of extracting nucleic acid from a biological sample utilizing principles of extraction enhancement and affinity exclusion to reduce heterogeneity in a sample containing a heterogeneous collection of nucleic acid-containing materials. A number of variations are possible, each of which is described below.

In all aspects of the invention as described herein, nucleic acid-containing materials refer to cells, microvesicles, RNA-protein complexes, and other nucleic acid-containing particles naturally found in biological samples. Examples of cells containing nucleic acids of special interest include, but are not limited to, circulating tumor cells and other cells that have undergone or are undergoing disease-related transformation, or other cells that contain genomic evidence of the physical status or health of an organism. Examples of microvesicles include, but are not limited to, exosomes, membrane vesicles, shedding microvesicles, microparticles, nanovesicles, apoptotic bodies, nanoparticles and membrane vesicles, and will collectively be referred to throughout this specification as "microvesicles" unless otherwise expressly denoted. Nucleic acid-containing materials may originate from, for example, a particular cell, organ or tissue of the body, or bodily fluid. For example, nucleic acid-containing materials can be detected or isolated from urine. Alternatively, a nucleic acid-containing material may originate from, for example, a tumor, hyperplastic growth, nodule, neoplasm, cyst, or mass. Nucleic acid-containing materials carry surface molecules, such as antigens, biomarkers, receptors, that may be used to identify, detect, isolate, enrich, or sort nucleic acid-containing materials from a specific donor cell type, tissue or organ of the body, or bodily fluid. Individual species of nucleic acid-containing materials may co-purify during extraction methods, as described herein. For example, circulating tumor cells may co-purify with microvesicles.

A "heterogeneous collection of nucleic acid-containing materials," as used herein, is a mixture of any of the foregoing species of nucleic acid-containing materials, e.g., cells, any species of microvesicle, RNA-protein complexes, and any other species of nucleic acid-containing particles, or any combination thereof. For example, a heterogeneous collection of nucleic acid-containing materials of the present invention includes cells or microvesicles, or both. In one aspect, a heterogeneous collection of nucleic acid-containing materials of the present invention is circulating tumor cells and microvesicles. In some embodiments, the mixture will comprise one or more cells in addition to any or all of the other species of nucleic acid-containing materials.

In one aspect, the invention is a method of extracting nucleic acid from a biological sample, comprising the steps of: obtaining a biological sample; performing a sample pre-processing step on the biological sample to obtain a fraction comprising a heterogeneous collection of nucleic acid-containing materials; performing an extraction enhancement operation; and extracting nucleic acid from the resulting materials. There is no specified order to the performance of the sample pre-processing step and the extraction enhancement operation, and indeed, the two may be performed simultaneously. Preferably, this method will result in a nucleic acid extraction that meets one or more of the quality standards described below in terms of the quantitative ratio of 18S rRNA to 28S rRNA, or nucleic acid yield. The heterogeneous collection of nucleic acid-containing materials includes, but is not limited to, a mixture of nucleic acid-containing materials, which include, but are not limited to, cells or microvesicles, or both.

In another aspect, the invention is a method of extracting nucleic acid from a biological sample, comprising the steps of: obtaining a biological sample; performing a sample pre-processing step on the biological sample to obtain a fraction comprising a heterogeneous collection of nucleic acid-containing materials; performing an affinity exclusion operation on the heterogeneous collection of nucleic acid-containing materials; and extracting nucleic acid from the resulting materials. Preferably, this method will result in a nucleic acid extraction that meets one or more of the quality standards described below in terms of the quantitative ratio of 18S rRNA to 28S rRNA, or nucleic acid yield. The heterogeneous collection of nucleic acid-containing materials includes, but is not limited to, a mixture of nucleic acid-containing materials, which include, but are not limited to, cells or microvesicles or both.

In yet another aspect, the invention is a method of extracting nucleic acid from a biological sample, comprising the steps of: obtaining a biological sample; performing a sample pre-processing step on the biological sample to obtain a fraction comprising a heterogeneous collection of nucleic acid-containing materials; performing an extraction enhancement operation; performing an affinity exclusion operation on the resulting materials; and extracting nucleic acid from the remaining materials. There is no specified order to the performance of the sample pre-processing step and the extraction enhancement operation, and indeed, the two may be performed simultaneously. The affinity exclusion operation is performed at any time after the pre-processing step. Preferably, this method will result in a nucleic acid extraction that meets one or more of the quality standards described below in terms of the quantitative ratio of 18S rRNA to 28S rRNA, or nucleic acid yield. The heterogeneous collection of nucleic acid-containing materials includes, but is not limited to, a mixture of nucleic acid-containing materials, which include, but are not limited to, cells or microvesicles, or both.

In a further aspect, the invention is a nucleic acid extraction from a heterogeneous collection of nucleic acid-containing materials obtained from a eukaryotic biological sample, wherein 18S rRNA and 28S rRNA are detectable in the extraction. Preferably, the quantitative ratio of 18S rRNA to 28S rRNA detectable in the nucleic acid extractions is within the range of approximately 1:1 to approximately 1:2; and is preferably approximately 1:2. Nucleic acid extractions of this nature are obtainable using any of the above-described methods.

In a further aspect, the invention is a nucleic acid extraction from a heterogeneous collection of nucleic acid-containing materials obtained from a bodily fluid sample with a protein concentration of less than 10 mg/ml, such as urine, where the nucleic acid extraction has a nucleic acid yield of great than or equal to 50 pg/ml from 20 ml of biological sample. Nucleic acid extractions of this nature are obtainable using any of the above-described methods.

In a still further aspect, the invention is a nucleic acid extraction from a heterogeneous collection of nucleic acid-containing materials obtained from a bodily fluid sample with a protein concentration of greater than 10 mg/ml, such as serum or plasma, wherein the nucleic acid extraction has a nucleic acid yield of greater than or equal to 50 pg/ml from 1 ml of biological sample. The heterogeneous collection of nucleic acid-containing materials includes, but is not limited to, a mixture of nucleic-acid containing materials, which include, but are not limited to, cells or microvesicles. Nucleic acid extractions of this nature are obtained by using any of the above-described methods.

In yet another aspect, nucleic acid profiles are obtained by analyzing the nucleic acid extractions resulting from any of the foregoing methods.

In a further aspect, the invention is a kit for extracting nucleic acids from biological samples or heterogeneous nucleic acid-containing collection. Embodiments, variations, and examples of which are described below. The heterogeneous collection of nucleic acid-containing materials includes, but is not limited to, a mixture of nucleic-acid containing materials, which include, but are not limited to, cells or microvesicles, or both.

All of the foregoing embodiments may include a sample pre-processing step which includes techniques for separating nucleic acid-containing materials from a biological sample. For example, methods of centrifugation, filtration concentration, and/or anion exchange and/or gel permeation chromatography can be used.

All of the foregoing embodiments may include an extraction enhancement operation step to remove or mitigate adverse factors that prevent high quality nucleic acid extraction from a biological sample. Extraction enhancement agents may include, but are not limited to, RNase inhibitor, protease, reducing agent, decoy substrate (e.g., synthetic RNA), soluble receptor, small interfering RNA, RNA binding molecule (e.g., anti-RNA antibody, chaperone protein, RNase inhibitory protein), or RNase denaturing substance (e.g., high osmolarity solution detergent), or any combination of the foregoing agents.

All of the foregoing embodiments may include an affinity exclusion operation, as described below, for reducing the heterogeneity of the fraction of nucleic acid-containing materials obtained from the preprocessing step. For example, the affinity exclusion operation may remove nucleic acid-containing materials that are not of interest. The depletion may be complete or partial. For example, in some instances a depletion of 50% of the undesirable materials would be sufficient to achieve a high quality nucleic acid extraction.

All of the foregoing embodiments may include an affinity enrichment operation, as described below, wherein affinity selection methods are used to enrich for nucleic acid-containing materials of a certain type or originating from a particular cell, tissue or organ of the body. For example, nucleic acid-containing materials from specific donor cells can be detected, selected, or enriched by the specific surface molecules known to be present.

In a further aspect, the invention provides a use for any of the nucleic acid extraction methods disclosed herein in any of a variety of known methods and techniques for analyzing nucleic acids in support of patient diagnostics, prognostics, theranostics, monitoring, predictive medicine, personalized medicine, integrated medicine, pharmacodiagnostics and diagnostic/prescription partnering (companion diagnostics). For example, the nucleic acid obtained from the practice of the extraction method is analyzed for the presence or absence of a genetic aberration associated with a disease or medical condition.

In any of the aspects of the present invention, a nucleic acid is, for example, DNA or RNA. The RNA can be, for example, coding RNA, e.g. messenger RNA which may encode proteins, or non-coding RNA (ncRNA), e.g., ribosomal RNA, transfer RNA, microRNA, and other non-coding transcripts that may originate from genomic DNA. Non-coding RNA transcripts may include, but are not limited to, transcripts that are transcribed from satellite repeats and transposons, which may be DNA transposons or retrotransposons. The DNA can be, for example, single stranded DNA, e.g. cDNA that is reverse transcribed from RNA or generated from DNA replication; double-stranded DNA; genomic DNA; non-coding DNA (ncDNA), e.g.

satellite repeats, transposons, or retrotransposons; or any fragment or combination thereof.

In any of the aspects of the present invention, the biological sample can be any sample from an organism, for example, a mammal, and in particular, a human. Preferably, the biological sample is a bodily fluid such as urine, blood, serum or plasma, and may also include sputum, spinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intraorgan system fluid, ascitic fluid, tumor cyst fluid, amniotic fluid and combinations thereof.

In any of the aspects of the present invention, a biological sample may come from a subject. Examples of subjects include, but are not limited to, all animals shown to or expected to have nucleic acid-containing materials. In particular embodiments, the subject is a mammal, a human or nonhuman primate, a dog, a cat, a horse, a cow, other farm animals, or a rodent (e.g. mouse, rat, guinea pig, etc.).

Other features and advantages of the invention will be apparent from and are encompassed by the following detailed description and claims.

DETAILED DESCRIPTION

Figure 1:
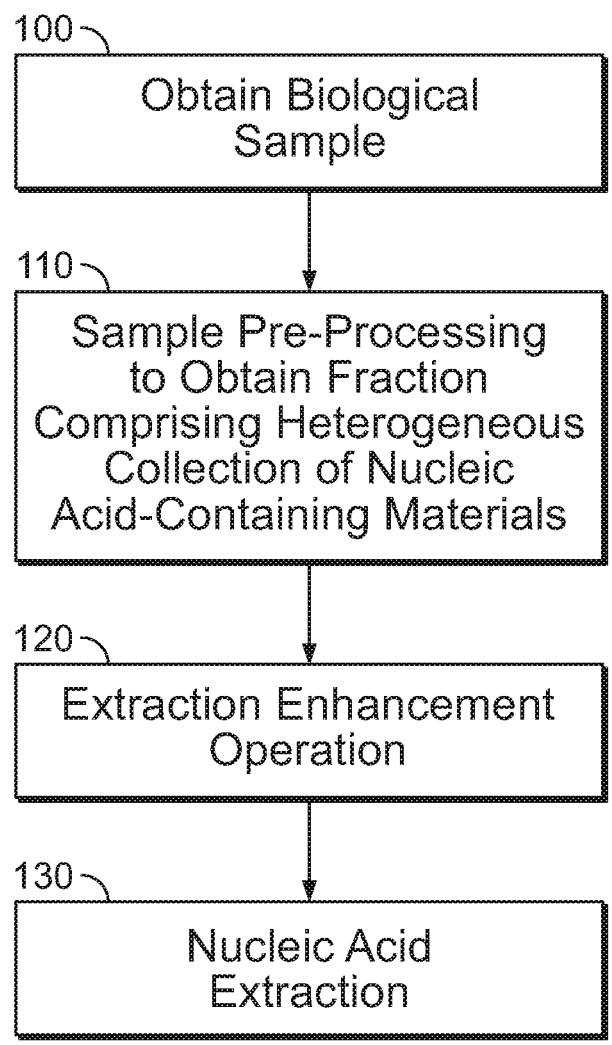
FIG. 1 is a flow chart depicting a first aspect of the present invention directed to a new method of nucleic acid extraction from a biological sample.

Nucleic Acid-Containing Materials and Heterogeneous Collections Thereof

Nucleic acid-containing biological materials are often used as starting materials for nucleic acid extraction and analysis. Cells are an example of a nucleic acid-containing biological material. Examples of cells containing nucleic acids of special interest include, but are not limited to, circulating tumor cells and other cells that have undergone or are undergoing disease-related transformation, or other cells that contain genomic evidence of the physical status or health of an organism. In addition, nucleic acids can be found in smaller materials ranging in size from about 10 nm in diameter to about 10000 nm in diameter. For example, "exosomes" have diameters of approximately 30 to 200 nm, with shedding microvesicles and apoptotic bodies often described as larger (Orozco and Lewis, 2010). Exosomes, shedding microvesicles, microparticles, nanovesicles, apoptotic bodies, nanoparticles and membrane vesicles co-isolate using various techniques and will, therefore, collectively be referred to throughout this specification as "microvesicles" unless otherwise expressly denoted. Other nucleic acid-containing materials, such as RNA-protein complexes, may co-isolate with cells and microvesicles using the various methods and techniques described herein. Accordingly, the generic term "nucleic acid-containing materials" will be used herein to refer to cells, microvesicles, RNA-protein complexes, and other nucleic acid containing particles naturally found in biological samples.

A "heterogeneous collection of nucleic acid-containing materials," as used herein, is a mixture of any of the foregoing species of nucleic acid-containing materials, e.g., cells, any species of microvesicle, RNA-protein complexes, and any other species of nucleic acid-containing particles. Preferably, the mixture will comprise one or more cells in addition to any or all of the other species of nucleic acid-containing materials.

Nucleic acid-containing materials may originate from particular cells, tissues or organs of the body, or bodily fluids. In particular, nucleic acid-containing materials may be isolated from urine, plasma, or serum. In some embodiments, nucleic acid-containing materials may originate from a tumor, hyperplastic growth, nodule, neoplasm, cyst, or mass. Nucleic acid-containing materials often carry surface molecules such as antigens, biomarkers, or receptors from their donor cells. These surface molecules may be used to detect, identify, isolate, sort, and/or enrich nucleic acid-containing materials from a specific donor cell type (Al-Nedawi et al., 2008; Taylor and Gercel-Taylor, 2008). In this way, nucleic acid-containing materials originating from distinct cell populations can be analyzed for their nucleic acid content. For example, tumor (malignant and non-malignant) nucleic acid-containing materials carry tumor-associated surface antigen and may be detected, isolated, or enriched via these specific tumor-associated surface antigens.

Nucleic Acid Extraction Methods

In a first embodiment, the invention is a method of extracting nucleic acid from a biological sample, comprising the steps of: obtaining a biological sample; performing a sample pre-processing step on the biological sample to obtain a fraction comprising a heterogeneous collection of nucleic acid-containing materials (preferably said heterogeneous collection comprises cells in addition to other nucleic acid-containing materials); performing an extraction enhancement operation; and extracting nucleic acid from the resulting materials. There is no specified order to the performance of the sample pre-processing step and the extraction enhancement operation, and indeed, the two may be performed simultaneously. Preferably, this method will result in a nucleic acid extraction that meets one or more of the quality standards described below in terms of the quantitative ratio of 18S rRNA to 28S rRNA, or nucleic acid yield.

One variation of this first embodiment is shown in FIG. 1, wherein the method comprises the steps of obtaining a biological sample (100), pre-processing the sample to obtain a fraction comprising a heterogeneous collection of nucleic acid-containing materials (110), performing an extraction enhancement operation on the fraction (120), and extracting nucleic acid from the fraction (130).

In variations of this first embodiment, the extraction enhancement operation is performed prior to the sample pre-processing, or the pre-processing and extraction enhancement operations are performed simultaneously.

In further variations, there may be an additional step of removing nucleic acids that are not located inside the cells or microvesicles that may be part of the heterogeneous collection of nucleic acid-containing materials. Methods of removing nucleic acids are well known in the art. For example, an enzyme digestion step may be performed at any point in the process, e.g., prior to sample pre-processing, prior to performance of the enhancement extraction operation, or prior to nucleic acid extraction. Such enzymes may be a type of ribonuclease that catalyzes the enzymatic digestion of ribonucleic acids or a type of deoxyribonuclease that catalyzes the enzymatic digestion of deoxyribonucleic acids.

The biological sample can be any sample from an organism, for example, a mammal, and in particular, a human. Preferably, the biological sample is a bodily fluid such as urine, blood, serum or plasma, and may also include sputum, spinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intraorgan system fluid, ascitic fluid, tumor cyst fluid, amniotic fluid and combinations thereof.

A biological sample may sometimes come from a subject. The term "subject" is intended to include all animals shown to or expected to have nucleic acid-containing materials. In particular embodiments, the subject is a mammal, a human or nonhuman primate, a dog, a cat, a horse, a cow, other farm animals, or a rodent (e.g. mouse, rat, guinea pig, etc.). The terms "subject," "individual" and "patient" are used interchangeably herein and have the same meaning.

The sample pre-processing step provides certain advantages not present in nucleic acid extraction methods of the prior art that do not employ a pre-processing step to obtain from the sample a fraction comprising a heterogeneous collection of nucleic acid-containing materials. For example, the methods of the present invention, employing as they all do, a pre-processing step, (1) tend to produce significantly higher yields of extracted nucleic acid with higher integrity; (2) provide advantages associated with scalability, e.g., when used in support of an assay to detect nucleic acids expressed in a subject at low levels, the sensitivity of the assay can be increased by isolating, in the pre-processing step, more nucleic acid-containing materials from a larger volume of sample fluid; (3) purer nucleic acids in that protein and lipids, debris from dead cells, and other potential contaminants and PCR inhibitors can be excluded from the nucleic acid-containing materials isolated in the preprocessing step; and (4) more choices in nucleic acid extraction tools and techniques as the fraction comprising nucleic acid-containing materials that results from the pre-processing step is typically of much smaller volume than the starting sample volume, making it possible to extract nucleic acids from the fraction using small volume tools and techniques such as small volume column filters.

The sample pre-processing step may be any of several known techniques for separating nucleic acid-containing materials from a biological sample. For example, a method of isolating circulating tumor cells is described in a paper by Stott et al. (Stott et al., 2010), a method of differential centrifugation is described in a paper by Raposo et al. (Raposo et al., 1996), a paper by Skog et. al. (Skog et al., 2008) and a paper by Nilsson et al. (Nilsson et al., 2009). Methods of anion exchange and/or gel permeation chromatography are described in U.S. Pat. Nos. 6,899,863 and 6,812,023. Methods of sucrose density gradients or organelle electrophoresis are described in U.S. Pat. No. 7,198,923. A method of magnetic activated cell sorting (MACS) is described in a paper by Taylor and Gercel-Taylor (Taylor and Gercel-Taylor, 2008). Methods of filtration concentration are described in a paper by Cheruvanky et al. (Cheruvanky et al., 2007) and in PCT Publication No. WO2011/009104 (Russo et al.). Further, microvesicles can be identified and isolated from bodily fluid of a subject by a newly developed microchip technology that uses a unique microfluidic platform to efficiently and selectively separate tumor-derived microvesicles (Chen et al., 2010). Each of the foregoing references is incorporated by reference herein for its teaching of these methods.

The purpose of the extraction enhancement step is to remove or mitigate adverse factors that prevent high quality nucleic acid extraction from a biological sample. In some biological samples, factors such as excessive circulating DNA may affect the quality of nucleic acid extraction from such samples and contaminate DNA extracted from within nucleic acid-containing materials. In other samples, factors such as excessive levels of endogenous RNase may affect the quality of nucleic acid extraction from such samples. Many agents and methods may be used to remove these adverse factors. These methods and agents are referred to collectively herein as an "extraction enhancement operation."

In some instances, the extraction enhancement operation may involve the addition of nucleic acid extraction enhancement agents to the biological sample or various derivatives of the sample at any given stage of the process. For the purpose of removing adverse factors such as endogenous RNase, extraction enhancement agents may include, but are not limited to, a commercially available RNase inhibitor such as Superase-In (Ambion Inc.), RNaseIN (Promega Corp.), or other agents that function in a similar fashion; a protease; a reducing agent; a decoy substrate such as a synthetic RNA; a soluble receptor that can bind RNase; a small interfering RNA (siRNA); an RNA binding molecule, such as an anti-RNA antibody, or a chaperone protein; an RNase denaturing substance, such as a high osmolarity solution, a detergent, or a combination thereof. These enhancement agents may exert their functions in various ways, for example, but not limited to, through inhibiting RNase activity (e.g., RNase inhibitors), through a ubiquitous degradation of proteins (e.g., proteases), or through a chaperone protein (e.g., a RNA-binding protein) that binds and protects RNA. In all instances, such extraction enhancement agents remove or mitigate some or all of the adverse factors in the biological sample that would otherwise prevent or interfere with the high quality extraction of nucleic acids from the sample.

In other instances, the extraction enhancement operation may involve the performance of one or more process steps. Such processes include extensive or substantially thorough washing of nucleic acid-containing components of the fraction or sample; size separation of RNases from the biological sample; denaturation of proteins in the biological sample by various techniques including, but not limited to, generating a particular pH condition, a temperature condition, (e.g., the maintenance of a decreasing or lower temperature), freeze/thaw cycles, and combinations thereof.

Thus, the extraction enhancement operation is comprised of: (a) the addition of one or more enhancement agents to the biological sample; or (b) the performance of one or more enhancement steps prior to nucleic acid extraction; or (c) a combination of enhancement agents and enhancement steps. The enhancement agents may include: (i) RNase inhibitor; (ii) protease; (iii) reducing agent; (iv) decoy substrate, such as synthetic RNA; (v) soluble receptor; (vi) small interfering RNA; (vii) RNA binding molecule, such as anti-RNA antibody, chaperone protein, or an RNase inhibitory protein; and (ix) RNase denaturing substance, such as high osmolarity solution or detergent. The extraction enhancement steps may include: (x) washing; (xi) size-separating RNase from the sample; (xii) effecting RNase denaturation through a physical change, such as by decreasing temperature, or executing a freeze/thaw cycle.

In variations in which the extraction enhancement operation involves the addition of an RNase inhibitor, the RNase inhibitor may be added to the biological sample or to the fraction comprising a heterogeneous collection of nucleic acid-containing materials prior to extracting nucleic acid. Preferably the RNase inhibitor has a concentration of greater than 0.027 AU (1×) for a sample equal to or more than 1 µl; alternatively, greater than or equal to 0.135 AU (5×) for a sample equal to or more than 1 µl; alternatively, greater than or equal to 0.27 AU (10×) for a sample equal to or more than 1 µl; alternatively, greater than or equal to 0.675 AU (25×) for a sample equal to or more than 1 µl; and alternatively, greater than or equal to 1.35 AU (50×) for a sample equal to or more than wherein the 1× protease concentration refers to an enzymatic condition wherein 0.027 AU or more protease is used to treat microvesicles isolated from 1 µl or more bodily fluid; the 5× protease concentration refers to an enzymatic condition wherein 0.135 AU or more protease is used to treat microvesicles isolated from 1 µl or more bodily fluid; the 10× protease concentration refers to an enzymatic condition wherein 0.27 AU or more protease is used to treat microvesicles isolated from 1 µl or more bodily fluid; the 25× protease concentration refers to an enzymatic condition wherein 0.675 AU or more protease is used to treat microvesicles isolated from 1 µl or more bodily fluid; the 50× protease concentration refers to an enzymatic condition wherein 1.35 AU or more protease is used to treat microvesicles isolated from or more bodily fluid. Preferably, the RNase inhibitor is a protease.

The nucleic acid extraction step may be performed using procedures that are well-known in the art. Persons of skill will select a particular extraction procedure as appropriate for the particular biological sample. Examples of extraction procedures are provided in patent publications WO/2009/100029 and WO/2011/009104, each of which is incorporated by reference herein for its teaching of these procedures as well as any other procedures mentioned herein. In some instances, with some techniques, it may also be possible to analyze the nucleic acid without first extracting it from the nucleic acid-containing materials.

In a second embodiment, the invention is a method of extracting nucleic acid from a biological sample, comprising the steps of: obtaining a biological sample; performing a sample pre-processing step on the biological sample to obtain a fraction comprising a heterogeneous collection of nucleic acid-containing materials; performing an affinity exclusion operation on the heterogeneous collection of nucleic acid-containing materials; and extracting nucleic acid from the resulting materials. The biological sample, pre-processing step, and nucleic acid extraction step are all as described above in relation to the first embodiment. Preferably, this method will result in a nucleic acid extraction that meets one or more of the quality standards described below in terms of the quantitative ratio of 18S rRNA to 28S rRNA, or nucleic acid yield.

Figure 2:
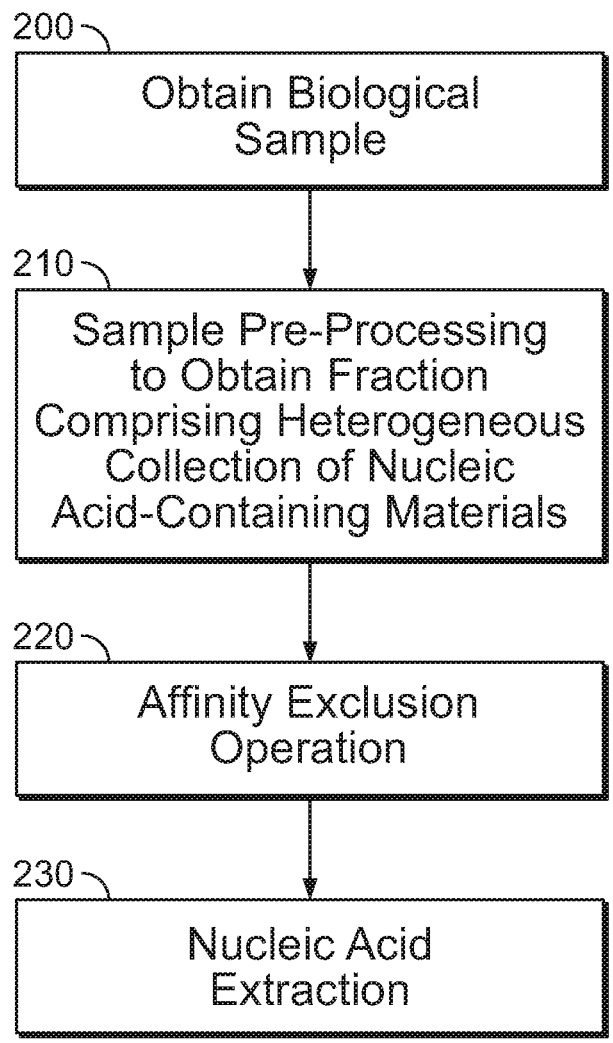
FIG. 2 is a flow chart depicting a second aspect of the present invention directed to a new method of nucleic acid extraction from a biological sample.

One variation of this second embodiment is shown in FIG. 2, wherein the method comprises the steps of obtaining a biological sample (200), pre-processing the sample to obtain a fraction comprising a heterogeneous collection of nucleic acid-containing materials (210), performing an affinity exclusion operation (220), and extracting nucleic acids from the affinity reduced fraction (230).

The affinity exclusion operation is a novel means for reducing the heterogeneity of the fraction of nucleic acid-containing materials obtained from the preprocessing step. Instead of using affinity selection techniques to enrich for nucleic-acid containing materials of interest, in the affinity exclusion operation, affinity techniques are used to remove nucleic-acid containing materials that are not of interest (e.g., nucleic acid containing materials originating from a cell type that is not of interest in a biomarker assay to be performed on the extracted nucleic acid). For example, using the methods and techniques described herein, epithelial cells, erythrocytes, leukocytes, neutrophils, lymphocytes, monocytes, basophils, thrombocytes, fibroblasts, and mesenchymal cells may be eliminated from the sample prior to execution of the nucleic acid extraction step. The depletion may be complete or partial. For example, in some instances a depletion of 50% of the undesirable materials would be sufficient to achieve a high quality nucleic acid extraction.

Because nucleic acid-containing materials often carry surface molecules such as antigens from their donor cells, surface molecules may be used to identify and deplete nucleic acid-containing materials originating from a specific donor cell type. In one example, the surface molecule used in the affinity exclusion operation is a molecule specific to cell type, e.g., but not limited to, any of the cell-type markers listed in Table 1. Alternatively, depending upon assay design, the surface molecule used in the affinity exclusion operation may be a surface molecule listed in Table 2 if nucleic acid-containing materials originating from a specific tumor cell type are to be excluded in the assay.

TABLE 1

Examples of Cell-Type Specific Markers.

| Cell types and Markers | References |
| --- | --- |
| I. For positive selection: | |
| A. Epithelial cell markers: | |
| CD51 | (Siegel et al., 2009) |
| Cytokeratin 8 | (Punnoose et al., 2010) |
| Cytokeratin 18 | (Punnoose et al., 2010) |
| Cytokeratin 19 | (Punnoose et al., 2010) |
| E-cadherin (CD324, Cadherin-1) | (Punnoose et al., 2010) |
| EpCAM (ESA; Epithelial cell adhesion molecule; CD326) | (Shmelkov et al., 2008) |
| Mucin 1 (EMA, Epithelial membrane antigen; CA15-3; CD227) | (Matthews et al., 1988) |
| ZO-1 | (Siegel et al., 2009) |
| II. For negative selection from urine samples | |
| A. Erythrocyte (RBC) markers: | |
| AE1 (Band 3) | (Ding et al., 2004) |
| BGP1 | (Lewis et al., 1988) |

TABLE 1-continued

Examples of Cell-Type Specific Markers.

| Cell types and Markers | References |
|---|---|
| CD47 | (Oldenborg et al., 2000) |
| Globin | (Min-Oo et al., 2004) |
| Glycophorin A (GPA) | (Shan et al., 1998; Telen and Chasis, 1990) |
| Rh polypeptides and Rh glycoprotein | (Agre et al., 1990; Avent et al., 1996) |
| TER119 | (Jiang et al., 2005; Kobayashi et al., 2004) |
| Transferrin receptor (CD71) | (Min-Oo et al., 2004; Tao et al., 2000) |
| B. Leukocyte (WBC) markers: | |
| Beta2 Leukocyte Integrins (CD11/CD18) | (Flaherty et al., 1997) |
| CD45RA/CD45RB/CD45RO | (Bembridge et al., 1993; Lai et al., 1991; Masuoka et al., 1992) |
| CD166 (ALCAM, activated leukocyte cell adhesion molecule) | (Lunter et al., 2005) |
| HLA (human leukocyte antigen) | (Guerini et al., 2006) |
| LAM-1 (leukocyte adhesion molecule-1) | (Kansas et al., 1991) |
| L-selectin | (Tu et al., 2002; Venturi et al., 2003) |
| LSP1 (leukocyte-specific protein-1) | (Hannigan et al., 2001; Marafioti et al., 2004) |
| Ly-9 | (de la Fuente et al., 2001) |
| M6 (leukocyte activation antigen) | (Kasinrerk et al., 1992) |
| III. For negative selection from blood samples | |
| A. Same as II A and II B | |
| B. Neutrophil markers: | |
| 31D8 | (Gallin et al., 1986; Spiekermann et al., 1996) |
| CD11b - also a monocyte marker | (De Clerck et al., 1995) |
| CD15 | |
| CD18 | (De Clerck et al., 1995) |
| CD45 | |
| CD64 | (Matsui et al., 2006) |
| Gelatinase | (Borregaard et al., 1995) |
| Mac-1 | |
| C. Lymphocyte markers: | |
| T-cells: CD3, CD5, T cell receptor (TCR) | (Berrington et al., 2005) |
| B-cells: MHC class II, CD19, CD21 | (Berrington et al., 2005) |
| NK-cells: CD16, CD56, NKp46, NKp44 | (Berrington et al., 2005) |
| D. Monocyte/Macrophase markers: | |
| 125I-WVH-1 | (Fayle et al., 1985) |
| CD11b - also a neutrophil marker | (Fink et al., 2003) |
| CD14 | (Jonas et al., 1990; Ruppert et al., 1991) |
| FcRI and FcRII | (Clement et al., 1985) |
| HLA-DR | |
| Ki-M1p | (Rudolph et al., 1997) |
| p-selectin | |
| E. Basophil markers: | |
| 2D7 | (Agis et al., 2006b; Kepley et al., 1995) |
| Basogranulin (BB1) | (Agis et al., 2006a) |
| Bsp-1 | (Valent et al., 1990) |
| CCR-3 (eotaxin receptor) | (Ducrest et al., 2005) |
| CD203-c (E-NPP3) | (Sainte-Laudy and Belon, 2006) |
| CDw-17 (lactosylceramide) | (Yokohama et al., 2002) |
| CD88 | (Yokohama et al., 2002) |
| F. Thrombocyte (platelet) marker: | |
| CD36 | (Thibert et al., 1995) |
| G. Dendritic cell marker: | |
| CD83 | |
| CD11c | |
| CD1a | |
| H. Endothelial cells | |
| CD31 | |
| IV. Other type markers | |
| A. Fibroblast marker: | |
| Fibroblast-specific protein 1 (FSP1) | (Nishitani et al., 2005; Strutz et al., 1995) |
| MAb AS02 | |
| Thy. 1 | |
| B. Mesenchymal marker: | |
| CD29 | (Siegel et al., 2009) |
| N-cadherin | (Li et al., 2011) |
| Vimentin | (Punnoose et al., 2010) |

TABLE 1-continued

Examples of Cell-Type Specific Markers.

| Cell types and Markers | References |
| --- | --- |
| C. Glioblastoma cells marker: | |
| EGFRvIII protein | (Al-Nedawi et al., 2008) |
| PDGFR | |
| IL13Ra2 | |
| CD133 | |
| chondroitin proteoglycan sulfate | |
| 3'-isoLM1 | |
| 3'6'-isoLD1 | |
| GPNMB | |
| MRP3 | |
| podoplanin | |
| D. HERV particle marker | |
| HERV env | |

In variations of this second embodiment, the method may additionally comprise an extraction enhancement operation, as described above in relation to the first embodiment. The extraction enhancement operation may be performed at any time in the process prior to the final nucleic acid extraction step.

In further variations, there may be an additional step of removing nucleic acids that are not located inside the cells or microvesicles that may be part of the heterogeneous collection of nucleic acid-containing materials. Methods of removing nucleic acids are well known in the art. For example, an enzyme digestion step may be performed at any point in the process. Such enzymes may be a type of ribonuclease that catalyzes the enzymatic digestion of ribonucleic acids or a type of deoxyribonuclease that catalyzes the enzymatic digestion of deoxyribonucleic acids.

In a third embodiment, the invention is a method of extracting nucleic acid from a biological sample, comprising the steps of: obtaining a biological sample; performing a sample pre-processing step on the biological sample to obtain a fraction comprising a heterogeneous collection of nucleic acid-containing materials; performing an extraction enhancement operation; performing an affinity exclusion operation; and extracting nucleic acid from the resulting materials. The biological sample, pre-processing step, extraction enhancement operation, affinity exclusion operation, and nucleic acid extraction step are all as described above in relation to the first and second embodiments.

In this embodiment, the sample pre-processing step must occur before the affinity exclusion operation, but the extraction enhancement operation may occur at any time prior to the nucleic acid extraction step.

Preferably, this embodiment too will result in a nucleic acid extraction that meets one or more of the quality standards described below in terms of the quantitative ratio of 18S rRNA to 28S rRNA, or nucleic acid yield.

Figure 3:
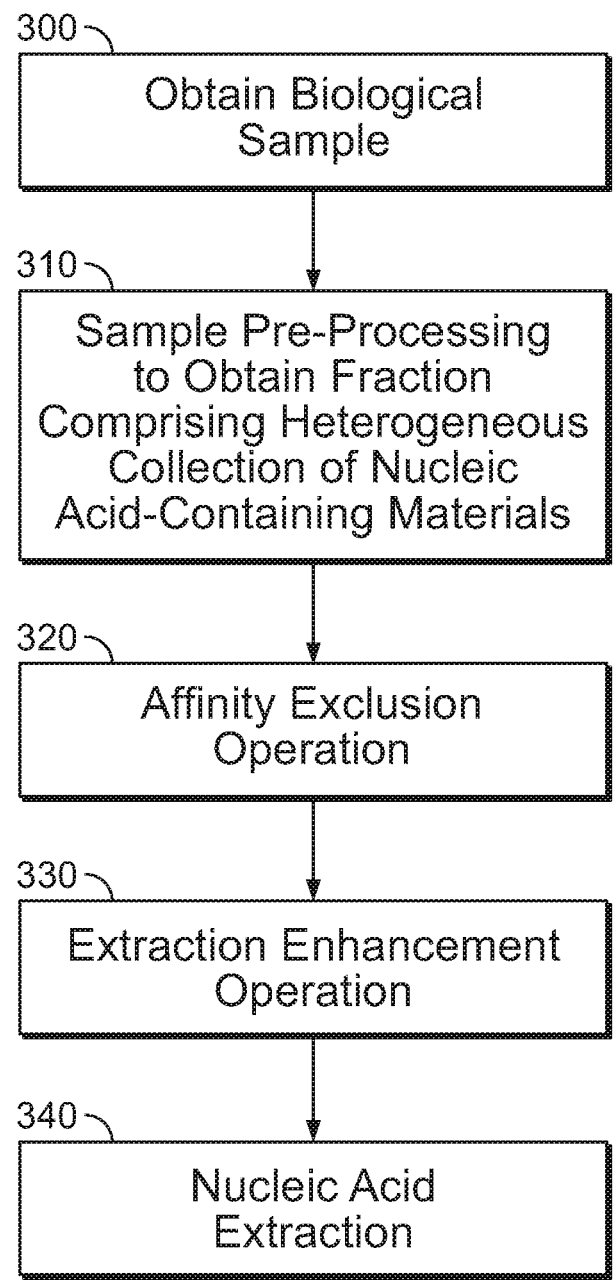
FIG. 3 is a flow chart depicting a third aspect of the present invention directed to a new method of nucleic acid extraction from a biological sample.

One variation of the method described in this embodiment is shown in FIG. 3, wherein the method comprises the steps of obtaining a biological sample (300), pre-processing the sample to obtain a fraction comprising a heterogeneous collection of nucleic acid-containing materials (310), performing an affinity exclusion operation (320), performing an extraction enhancement operation (330), and extracting nucleic acids.

As with the first and second embodiments, this third embodiment may further comprise an additional step of removing nucleic acids that are not located inside the cells or microvesicles that may be part of the heterogeneous collection of nucleic acid-containing materials. Methods of removing nucleic acids are well known in the art. For example, an enzyme digestion step may be performed at any point in the process, e.g., prior to sample preprocessing, prior to performance of the enhancement extraction operation, or prior to nucleic acid extraction. Such enzymes may be a type of ribonuclease that catalyzes the enzymatic digestion of ribonucleic acids or a type of deoxyribonuclease that catalyzes the enzymatic digestion of deoxyribonucleic acids.

Affinity Enrichment

All of the foregoing embodiments and variations of the nucleic acid extraction methods described above may further comprise an affinity enrichment operation, wherein affinity selection methods are used to enrich for nucleic acid-containing materials of a certain type or originating from a particular cell, tissue or organ of the body, e.g., lung, pancreas, stomach, intestine, bladder, kidney, ovary, testis, skin, colorectal, breast, prostate, brain, esophagus, liver, placenta, or fetus cells.

Because the nucleic acid-containing materials often carry surface molecules such as antigens from their donor cells, surface molecules may be used to identify, isolate and/or enrich for nucleic acid-containing materials from a specific donor cell type (Al-Nedawi et al., 2008; Taylor and Gercel-Taylor, 2008). In this way, nucleic acid-containing materials originating from distinct cell populations can be analyzed for their nucleic acid content. For example, tumor (malignant and non-malignant) nucleic acid-containing materials carry tumor-associated surface antigens and may be detected, isolated, or enriched via these specific tumor-associated surface antigens.

In one example, the surface antigen is epithelial-cell-adhesion-molecule (EpCAM), which is specific to nucleic acid-containing materials from carcinomas of lung, colorectal, breast, prostate, head and neck, and hepatic origin, but not of hematological cell origin (Balzar et al., 1999; Went et al., 2004).

In another example, the surface antigen is CD24, which is a glycoprotein specific to urine nucleic acid-containing materials (Keller et al., 2007).

In yet another example, the surface antigen is selected from a group of molecules such as CD70, carcinoembryonic antigen (CEA), EGFR, EGFRvIII and other variants, Fas ligand, TRAIL, transferrin receptor, p38.5, p97 and HSP72. Additionally, tumor specific nucleic acid-containing materials may be characterized by the lack of surface markers, such as CD80 and CD86.

In further examples, the surface antigens are any one of the tumor markers, listed in Table 2. The surface antigens in Table 2 may be used to perform an affinity enrichment operation so that nucleic acid-containing materials from a specific tumor cell type are enriched. Alternatively, depending upon the assay design, the surface antigen in the affinity enrichment operation may be any of the surface markers listed in the foregoing Table 1.

TABLE 2

Examples of Tumor Biomarkers

| BIOMARKER | NAME(S) | COMBINATION | CANCER TYPE | REFERENCES |
|---|---|---|---|---|
| ABCB1 | MDR1; P-glycoprotein 1; ATP-binding cassette sub-family B member 1 | | Acute myeloid leukemia (AML), Pancreas Ovary | (Young, 2007) (Fong and Kakar, 2010) |
| ABCB5 | ATP-binding cassette sub-family B member 5 | | Melanoma | (Schatton et al., 2008) |
| ABCG2 | CDw338; BCRP; ATP-binding cassette subfamily G member 2 | | Breast Ovary | (Kim et al., 2002) (Fong and Kakar, 2010) |
| AFP | Alpha-fetoprotein | | Hepatocellular | (Baig et al., 2009) |
| ALDH1 | Aldehyde dehydrogenase 1 | ALDH1+/CD44+/CD24−/lin− | Breast | (Ginestier et al., 2007) |
| ALDH1 | Aldehyde dehydrogenase 1 | | Hematopoietic Lung | (Matsui et al., 2004) (Jiang et al., 2009) |
| APOE | Apolipoprotein E, apo E | | Ovary | (Chen et al., 2005) |
| BIRC5 | Survivin; baculoviral inhibitor of apoptosis repeat-containing 5 | | Lung | (Falleni et al., 2003) |
| CD15 | leuM1; 3-fucosyl-N-acetyl-lactosamine | | Breast, colorectal, leukemia, lung | (Ball, 1995) |
| CD20 | B-lymphocyte antigen 20 | | B-cell lymphoma, leukemia | (Coiffier, 2007) |
| CD24 | HSA; heat stable antigen CD24 | CD24+/CD44+/EpCAM+ | Pancreas | (Li et al., 2007) |
| CD24 | HSA; heat stable antigen CD24 | | Colon, gallbladder, ovary, pancreas, stomach | (Lim and Oh, 2005; Sagiv et al., 2006) |
| CD34 | CD34 molecule; Hematopoietic progenitor cell antigen CD34 | CD34+/CD10−CD34+/CD38− | Leukemia AML | (Cox et al., 2004) (Kojima and Kitamura, 1999) |
| CD44 | CD44 molecule (Indian blood group) | CD44+/CD24−/low CD44+/CD24−/low/lin− CD44+/CD24− CD44+/CD24− CD44+/CD24− CD44+/CD24 low/EpCAM+ CD44+/EpCA M+ CD44+/MYD8 8+ CD44+/CD117 +/CD133+ CD44+/K5+/K20− CD44+/CD44v 6+/EMA− | Breast Breast Gliomas AML Prostate Breast Colon Ovary Bladder Bladder | (Al-Hajj et al., 2003) (Al-Hajj et al., 2003) (Galli et al., 2004; Hemmati et al., 2003; Ignatova et al., 2002; Lee et al., 2006; Singh et al., 2003; Singh et al., 2004; Uchida et al., 2000; Yuan et al., 2004) (Bonnet and Dick, 1997; Ishikawa et al., 2007; Lapidot al., 1994) (Hurt et al., 2008) (Fillmore and Kuperwasser, 2008) |

TABLE 2-continued

Examples of Tumor Biomarkers

| BIOMARKER | NAME(S) | COMBINATION | CANCER TYPE | REFERENCES |
| --- | --- | --- | --- | --- |
| | | | | (Boman and Huang, 2008) (Alvero et al., 2009) (Fong and Kakar, 2010) (Chan et al., 2009) (Yang and Chang, 2008) |
| CD44 | CD44 molecule (Indian blood group) | | AML Head and neck | (Jin et al., 2006) (Prince et al., 2007) |
| CD47 | MER6; IAP; immunoglobulin-like transmembrane integrin-associated protein | | Bladder | (Chan et al., 2009) |
| CD90 | Thy-1, thymocyte differentiation antigen 1 | CD90+/CD44+ | Liver | (Yang et al., 2008) |
| CD96 | CD96; Tactile; T-cell activation increased late expression | | Leukemia | (Hosen et al., 2007) |
| CD133 | PROM1, prominin-1 | CD133+/ABCG2+ CD133+/CD44+ | Melanoma Colon | (Monzani et al., 2007) (Dallas et al., 2009) |
| CD133 | PROM1, prominin-1 | | Brain Colon Hepatocellular Lung Ovary Pancreas Prostate Skin | (Bao et al., 2006a; Hemmati et al., 2003; Liu et al., 2006; Singh et al., 2003; Singh et al., 2004; Taylor et al., 2005; Zeppernick et al., 2008) (O'Brien et al., 2007; Ricci-Vitiani et al., 2007; Todaro et al., 2007) (Smith et al., 2008) (Eramo et al., 2008) (Fernandina et al., 2008) (Hermann et al., 2007; Li et al., 2007) (Collins et al., 2005) (Monzani et al., 2007) |
| CD142 | Tissue factor; platelet tissue factor; factor III; thrombokinase | | Breast, colorectal, lung, pancreas | (Zwicker et al., 2009) |
| CD147 | EMMPRIN; extracellular matrix metalloproteinase inducer; basigin | | Prostate | (Zhong et al., 2011) |
| CD326 | CD326; Flotillin | | Breast, colon, GI, ovary Prostate | (Naundorf et al., 2002) (Oberneder et al., 2006) |

TABLE 2-continued

Examples of Tumor Biomarkers

| BIOMARKER | NAME(S) | COMBINATION | CANCER TYPE | REFERENCES |
|---|---|---|---|---|
| CEA | Carcinoembryonic antigen | | Colon | (Thomas et al., 2009) |
| CLDN3 | Claudin 3 | | Ovary | (Hough et al., 2001; Rangel et al., 2003) |
| CLDN4 | Claudin 4 | | Ovary | (Hough et al., 2001; Rangel et al., 2003) |
| CLDN7 | Claudin 7 | | Ovary | (Hough et al., 2001) |
| CTSB | Cathepsin B | | Glioma | (Strojnik et al., 2007) |
| CXCL1 | GRO-alpha; Chemokine (C-X-C motif) ligand 1 | | Bladder | (Kawanishi et al., 2008) |
| CXCR4 | Chemokine receptor type 4 | | Colon Gliomas Melanoma Prostate | (Ottaiano et al., 2005) (Dirks, 2001; Liu et al., 2006; Salmaggi et al., 2006) (Alsayed et al., 2007) (Sun et al., 2005) |
| EpCAM | ESA; Epithelial cell adhesion molecule; CD326 | EpCAM+/CD45− | Breast, colorectal, prostate | (Allard et al., 2004) |
| EpCAM | ESA; Epithelial cell adhesion molecule; CD326 | | Colon, prostate | (Ammons et al., 2003; Goel et al., 2007; Oberneder et al., 2006) |
| EGFR1 | erbB-1; HER1; Epidermal growth factor receptor 1 | | Anal Breast Glioblastoma Lung | (Walker et al., 2009) (Neve et al., 2006) (Heimberger et al., 2005) (Jackman et al., 2009; Punnoose et al., 2010) |
| EGFRvIII | Mutant EGFR | | GBM | (Pelloski et al., 2007) |
| FOLH1 | Folate hydrolase 1; PSM; PSMA, Prostate specific membrane antigen | | Prostate | (Chang et al., 1999; Ross et al., 2003) |
| FOLR1 | Folate receptor alpha | | Ovary | (Kalli et al., 2008) |
| | GDIa ganglioside | | Ovary | (Prinetti et al., 2010) |
| GFAP | Glial fibrillary acidic protein | | Glioblastoma | (Hill et al., 2003) |
| GYPA | Glycophorin A; CD235a | | Leukemia | (Andersson et al., 1979) |
| HER2 | erbB-2; neu; Human epidermal growth factor receptor 2 | | Breast Uterus | (Korkaya et al., 2008) (Santin et al., 2008) |
| HLA-G | Human leukocyte antigen-G | | Ovary | (Sheu and Shih Ie, 2007) |
| HPN | Hepsin; TMPRSS1 | | Prostate | (Dhanasekaran et al., 2001) |
| KLK2 | Kallikrein 2 | | Prostate | (Magklara et al., 1999; Partin et al., 1999; Rittenhouse et al., 1998) |
| KLK3 | PSA; Kallikrein 3; prostate specific antigen | | Prostate | (Rittenhouse et al., 1998) |

TABLE 2-continued

Examples of Tumor Biomarkers

| BIOMARKER | NAME(S) | COMBINATION | CANCER TYPE | REFERENCES |
|---|---|---|---|---|
| KLK5 | Kallikrein 5 | | Ovary | (Yousef et al., 2003a; Yousef et al., 2003b) |
| KLK6 | Kallikrein 6 | | Ovary | (Yousef et al., 2003b) |
| KLK7 | Kallikrein 7 | | Ovary | (Yousef et al., 2003b) |
| KLK8 | Kallikrein 8 | | Ovary | (Hoffman et al., 2002; Yousef et al., 2003b) |
| KLK10 | Kallikrein 10 | | Ovary | (Luo et al., 2001; Yousef et al., 2003b) |
| KLK11 | Kallikrein 11 | | Ovary | (Yousef et al., 2003b) |
| KLK14 | Kallikrein 14 | | Breast Ovary | (Borgono et al., 2003) (Borgono et al., 2003; Yousef et al., 2003b) |
| | Keratane sulfates | | Papillary thyroid carcinoma | (Magro et al., 2003) |
| L1CAM | CD171; L1 cell adhesion molecule | | Gliomas | (Bao et al., 2008) |
| LMP1 | EBV latent membrane protein 1 | | Lymphoblastoma | (Flanagan et al., 2003) |
| MET | c-Met; HGFR; hepatocyte growth factor receptor | | Breast | (Neve et al., 2006) |
| MSLN | Mesothelin | | Mesothelioma Ovary Pancreas | (Chang and Pastan, 1996) (Chang and Pastan, 1996; Lu et al., 2004) (Agarwal et al., 2008) |
| MUC 1 | Mucin 1; CD227 | | Breast Colon | (McGuckin et al., 1995; Taylor-Papadimitriou et al., 1999) (Niv, 2008) |
| MUC4 | Mucin 4 | | Ovary | (Shih Ie and Davidson, 2009) |
| MUC16 | Mucin 16; CA 125 ovarian cancer antigen | | Ovary | (Yin et al., 2002; Yin and Lloyd, 2001) |
| OPN | BSP-1; BNSP; Osteopontin; bone sialoprotein I | | Ovary | (Rosen et al., 2005; Visintin et al., 2008) |
| PCA-3 | DD3; Prostate cancer antigen 3 | | Prostate | (Laxman et al., 2008) |
| PNCAM | Polysialic acid or polysialylated NCAM (a posttranslational modification of NCAM, neural cell adhesion molecule) | | Prolactinoma Neuroendocrine Small-cell lung carcinoma | (Gurlek et al., 2007) (Figarella-Branger et al., 1990; Jin et al., 1991) (Komminoth et al., 1991) |
| PTK7 | Protein tyrosine kinase 7 | | T-cell acute lymphoblastic leukemia | (Shangguan et al., 2008) |
| TMPRSS2:ERG | Transmembrane protease, serine 2: Ets related gene | | Prostate | (Hessels et al., 2007; Laxman et al., 2008) |
| VEGF | Vascular endothelial growth factor | | Gliomas | (Bao et al., 2006b) |

One of skill in the art will appreciate that the surface markers described in Tables 1 and 2 may be used interchangeably for an affinity exclusion operation or an affinity enrichment operation depending on the objectives of a given assay and nucleic acid extraction method practiced according to the teachings of this disclosure. For example, on the one hand, the surface markers for fibroblasts may be used to exclude fibroblast-derived nucleic acid-containing materials when a procedure for evaluating glioblastoma biomarkers is performed. On the other hand, the surface markers for fibroblasts may be used to enrich fibroblast-derived nucleic acid-containing materials when a procedure for evaluating fibroblastoma is performed.

An affinity procedure for depletion or enrichment of nucleic acid-containing materials from a specific cell type may be accomplished, for example, by using antibodies, aptamers, aptamer analogs or molecularly imprinted polymers specific for a desired surface antigen (hereinafter "affinity agent(s)"). In one embodiment, the surface antigen is specific for a cancer type. In another embodiment, the surface antigen is specific for a cell type which is not necessarily cancerous.

One example of a method of nucleic acid-containing material separation based on cell surface antigen is provided in U.S. Pat. No. 7,198,923. There CD81 antibody was used to enrich CD81 antigen-containing exosomes to prepare HCV RNA from a blood sample.

Another example is described in, e.g., U.S. Pat. Nos. 5,840,867 and 5,582,981, WO/2003/050290 and a publication by Johnson et al. (Johnson et al., 2008). There, aptamers and their analogs that specifically bind surface molecules were used as a separation tool for enriching cell type-specific nucleic acid-containing materials. In addition, molecularly imprinted polymers may also specifically recognize surface molecules as described in, e.g., U.S. Pat. Nos. 6,525,154, 7,332,553 and 7,384,589 and a publication by Bossi et al. (Bossi et al., 2007) and may also be a tool for retrieving and isolating cell type specific nucleic acid containing materials. Each of the foregoing references is incorporated herein for its teaching of these methods.

Quality Standards for Nucleic Acid Extractions

The nucleic acid extractions obtained by the novel methods described herein are characterized by high yield and high integrity, making the extracted nucleic acids useful for various applications in which high quality nucleic acid extractions are required or preferred.

As mentioned above, the performance of any of the various nucleic acid extraction methods according to the present invention preferably results in a nucleic acid extraction that meets one or more of the quality standards described below in terms of the quantitative ratio of 18S rRNA to 28S rRNA, or nucleic acid yield.

Preferably, the nucleic acid extraction methods of this invention will result in a nucleic acid extraction in which one can detect significant quantities of ribosomal RNA (rRNA), specifically 18S and 28S rRNA, preferably in a ratio of approximately 1:1 to approximately 1:2; and more preferably, in a ratio of approximately 1:2.

Further, the nucleic acid extraction methods of the present invention will preferably result in improved yields of extracted nucleic acid. For example, using the methods described herein, one may obtain a nucleic acid yield of greater than or equal to 50 pg/ml from a 20 ml low protein biological sample such as urine. Alternatively, one may obtain a nucleic acid yield of greater than or equal to 50 pg/ml from 1 ml of a high protein biological sample, such as serum or plasma.

Thus, the novel nucleic acid extractions obtained by the methods described herein preferably meet one or more of the following quality standards: (1) the detection of 18S and 28S rRNA, preferably in a ratio of approximately 1:1 to approximately 1:2; and more preferably, approximately 1:2; and/or (2) a nucleic acid yield of greater than or equal to 50 pg/ml from a 20 ml low protein biological sample or a 1 ml high protein biological sample.

Use of the nucleic acid extraction methods, and resulting nucleic acid extractions, in nucleic acid analysis for research and clinical applications.

The nucleic acid extraction methods of the present invention may be used to produce novel and improved nucleic acid extractions for various applications, including but not limited to analysis of nucleic acid for research (e.g., research in support of the discovery of new biomarkers or biomarker associations) or clinical analysis of nucleic acid in aid of patient diagnostics, prognostics, theranostics, monitoring, predictive medicine, personalized medicine, integrated medicine, pharmacodiagnostics and diagnostic/prescription partnering (companion diagnostics).

In one embodiment, the extracted nucleic acids, including DNA and/or RNA, are analyzed directly without an amplification step. Direct analysis may be performed with different methods including, but not limited to, nanostring technology. NanoString technology enables identification and quantification of individual target molecules in a biological sample by attaching a color coded fluorescent reporter to each target molecule. This approach is similar to the concept of measuring inventory by scanning barcodes. Reporters can be made with hundreds or even thousands of different codes allowing for highly multiplexed analysis. The technology is described in a publication by Geiss et al. (Geiss et al., 2008) and is incorporated herein by reference for this teaching.

In another embodiment, it may be beneficial or otherwise desirable to amplify the nucleic acid prior to analyzing it. Methods of nucleic acid amplification are commonly used and generally known in the art, many examples of which are described herein. If desired, the amplification can be performed such that it is quantitative. Quantitative amplification will allow quantitative determination of relative amounts of the various nucleic acids, to generate a profile as described below.

In one embodiment, the extracted nucleic acid is RNA. The RNA is then preferably reverse-transcribed into complementary DNA (cDNA) before further amplification. Such reverse transcription may be performed alone or in combination with an amplification step. One example of a method combining reverse transcription and amplification steps is reverse transcription polymerase chain reaction (RT-PCR), which may be further modified to be quantitative, e.g., quantitative RT-PCR as described in U.S. Pat. No. 5,639,606, which is incorporated herein by reference for this teaching.

Nucleic acid amplification methods include, without limitation, polymerase chain reaction (PCR) (U.S. Pat. No. 5,219,727) and its variants such as in situ polymerase chain reaction (U.S. Pat. No. 5,538,871), quantitative polymerase chain reaction (U.S. Pat. No. 5,219,727), nested polymerase chain reaction (U.S. Pat. No. 5,556,773), self-sustained sequence replication and its variants (Guatelli et al., 1990), transcriptional amplification system and its variants (Kwoh et al., 1989), Qb Replicase and its variants (Miele et al., 1983), cold-PCR (Li et al., 2008), or any other nucleic acid amplification methods, followed by the detection of the amplified molecules using techniques well known to those of skill in the art. Especially useful are those detection schemes designed for the detection of nucleic acid molecules if such molecules are present in very low numbers. The foregoing references are art.

The analysis of nucleic acids present in the nucleic acid-containing materials may be quantitative and/or qualitative. For quantitative analysis, the amounts (expression levels), either relative or absolute, of specific nucleic acids of interest within the nucleic acid-containing materials are measured with methods known in the art (described below). For qualitative analysis, the species of specific nucleic acids of interest within the nucleic acid-containing materials, whether wild type or variants, are identified with methods known in the art.

Nucleic Acid Profiles

The invention further includes a novel, high-quality profile of nucleic acids from a biological sample. Such profiles are generated by performing any of the various embodiments and variations of the nucleic acid extraction methods disclosed herein, and analyzing the resulting nucleic acid.

A profile, as the term is used herein, refers to a collection of characteristics, which can be determined through the quantitative or qualitative analysis of one or more biological components or materials (such as nucleic acid) contained in a sample (such as a nucleic acid extraction obtained by any of the methods disclosed herein). A reference profile is a profile obtained from an independent subject or from the same subject at a different time point.

The nucleic acids of the profile can be RNA. RNA can be coding RNA, e.g., messenger RNA which may encode proteins. RNA can also be non-coding RNA (ncRNA), e.g., ribosomal RNA, transfer RNA, microRNA, and other non-coding transcripts that may originate from genomic DNA. These non-coding RNA transcripts may include transcripts that are transcribed from satellite repeats and transposons, which may be DNA transposons or retrotransposons.

The nucleic acids can also be DNA. DNA can be single-stranded DNA, e.g., cDNA, that is reverse transcribed from RNA. The DNA can also be single-stranded DNA that is generated during DNA replication. Genomic DNA replicates in the nucleus while the cell is dividing. Some of the replicated DNA may come off its template, be exported out of nucleus, and packaged in microvesicles. It is also possible for the DNA to be double-stranded DNA. In addition, the DNA can be non-coding DNA (ncDNA).

High quality nucleic acid profiles are highly desirable for many uses, such as for research (e.g., research in support of the discovery of new biomarkers or biomarker associations) or clinical uses such as patient diagnostics, prognostics, theranostics, monitoring, predictive medicine, personalized medicine, integrated medicine, pharmacodiagnostics and diagnostic/prescription partnering (companion diagnostics). It is desirable in that such profiles are consistent between samples. Such consistency cannot be achieved without high quality nucleic acid extractions.

In one embodiment, the nucleic acid profile includes one or more genetic aberrations, which is used herein to refer to nucleic acid amounts as well as nucleic acid variants. Preferably, the nucleic acid is endogenous to the subject. Genetic aberrations include, without limitation, over-expression of one or more genomic elements, underexpression of one or more genomic elements, alternative production of splice variants of one or more genomic elements, copy number variants (CNV) of one or more genomic elements (e.g. DNA double minutes) (Hahn, 1993), nucleic acid modifications (e.g., methylation, acetylation and phosphorylations), single nucleotide polymorphisms (SNPs), chromosomal rearrangements (e.g., inversions, deletions and duplications), and mutations (insertions, deletions, duplications, missense, nonsense, synonymous or any other nucleotide changes) of one or more genomic elements, which mutations, in many cases, ultimately affect the activity and function of the genome, lead to alternative transcriptional splice variants and/or changes of gene expression level.

The nucleic acids in the nucleic acid-containing materials can be any type of nucleic acid, including but not limited to the examples provided herein. In the category of RNA, the nucleic acids can be coding RNA, e.g., messenger RNA which may encode proteins; non-coding RNA (ncRNA), e.g., ribosomal RNA, transfer RNA, microRNA, and other non-coding transcripts that may originate from genomic DNA. Non-coding RNA transcripts may include transcripts that are transcribed from satellite repeats and transposons, which may be DNA transposons or retrotransposons. In the category of DNA, the nucleic acids can include single-stranded DNA (ssDNA), e.g., cDNA, which is reverse transcribed from RNA and ssDNA that is generated during DNA replication; double-stranded DNA (dsDNA); DNA that codes for proteins (coding DNA); and DNA that does not code for proteins, i.e., non-coding DNA (ncDNA).

The determination of such genetic aberrations can be performed by a variety of techniques known to the skilled practitioner. For example, expression levels of nucleic acids, alternative splicing variants, chromosome rearrangement and gene copy numbers can be determined by microarray analysis (U.S. Pat. Nos. 6,913,879, 7,364,848, 7,378,245, 6,893,837 and 6,004,755) and quantitative PCR. Particularly, copy number changes may be detected with the Illumina Infinium II whole genome genotyping assay or Agilent Human Genome CGH Microarray (Steemers et al., 2006). Nucleic acid modifications can be assayed by methods described in, e.g., U.S. Pat. No. 7,186,512 and patent publication WO/2003/023065. Particularly, methylation profiles may be determined by, e.g., the Illumina DNA Methylation OMA003 Cancer Panel. SNPs and mutations can be detected by hybridization with allele-specific probes, enzymatic mutation detection, chemical cleavage of mismatched heteroduplex (Cotton et al., 1988), ribonuclease cleavage of mismatched bases (Myers et al., 1985), mass spectrometry (U.S. Pat. Nos. 6,994,960, 7,074,563, and 7,198,893), nucleic acid sequencing, single strand conformation polymorphism (SSCP) (Orita et al., 1989), denaturing gradient gel electrophoresis (DGGE)(Fischer and Lerman, 1979a; Fischer and Lerman, 1979b), temperature gradient gel electrophoresis (TGGE) (Fischer and Lerman, 1979a; Fischer and Lerman, 1979b), restriction fragment length polymorphisms (RFLP) (Kan and Dozy, 1978a; Kan and Dozy, 1978b), oligonucleotide ligation assay (OLA), allele-specific PCR (ASPCR) (U.S. Pat. No. 5,639,611), ligation chain reaction (LCR) and its variants (Abravaya et al., 1995; Landegren et al., 1988; Nakazawa et al., 1994), flow-cytometric heteroduplex analysis (WO/2006/113590) and combinations or modifications thereof. Notably, gene expression levels may be determined by the serial analysis of gene expression (SAGE) technique (Velculescu et al., 1995). In general, the methods for analyzing genetic aberrations are reported in numerous publications, not limited to those cited herein, and are available to skilled practitioners. The appropriate method of analysis will depend upon the specific goals of the analysis, the condition/history of the patient, and the specific cancer(s), diseases or other medical conditions to be detected, monitored or treated. The forgoing references are incorporated herein for their teachings of these methods.

Kits for Obtaining Nucleic Acids

The present invention is also directed to a kit for obtaining nucleic acids from biological samples. The kit may comprise an affinity agent; an extraction enhancement agent; and a lysis buffer. In some embodiments, the affinity agent is capable of binding to one or more markers listed in Table 1 or Table 2.

In some instances, the kit may further comprise instructions for using the kit. Instructions for using the kit may be put in the package with the other kit components or in a different location accessible to a kit user (e.g., on a website or webpage accessible to the kit purchaser). The content of the instructions may include, but is not limited to, instructions for how to use the affinity agent, how to perform an affinity exclusion operation, how to reconstitute reagents, how to do the nucleic acid enhancement, how to use the lysis buffer, and how to carry out the whole procedure of obtaining nucleic acids by using the kit.

In some embodiments of the kit, the extraction enhancement agent may be RNase inhibitor; protease; reducing agent; decoy substrate; soluble receptor; small interfering RNA; RNA binding molecule; RNase denaturing substance; or any combination of any of the foregoing.

In some embodiments, affinity agent is suitable for performing an exclusion operation, and instructions included in or with the kit comprise instructions for using the affinity agent in an affinity exclusion operation. Kits of this nature may further comprise a second affinity agent, and instructions for using the second affinity agent in an affinity enrichment operation.

In additional embodiments, the kit may further comprise DNase, RNase, or both, and instructions for their use. These reagents may be used to eliminate DNA or RNA that is of no interest in the intended assay, e.g., DNA or RNA that clings to the outside of the nucleic acid-containing materials in the extraction. The amount of DNase or RNase may depend on the source of the biological sample. In some samples, the amount of DNA or RNA of no interest is relatively high, and therefore, more DNase or RNase will need to be added in the extraction process.

It should be understood that this invention is not limited to the particular methodologies, protocols and reagents, described herein, which may vary. The terminology used herein is for the purpose of describing particular embodiments only, and is not intended to limit the scope of the present invention, which is defined solely by the claims.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

EXAMPLES

Example 1

Nucleic Acid Extraction with Extraction Enhancement Operation

One variation of the invention is shown in FIG. 1, where the method comprises the steps of obtaining a biological sample (100), pre-processing the sample to obtain a fraction comprising a heterogeneous collection of nucleic acid-containing materials (110), performing an extraction enhancement operation on the fraction (120), and extracting nucleic acid from the fraction (130).

Example 2

Nucleic Acid Extraction with Affinity Exclusion Operation

One variation of the invention is shown in FIG. 2, where the method comprises the steps of obtaining a biological sample (200), pre-processing the sample to obtain a fraction comprising a heterogeneous collection of nucleic acid-containing materials (210), performing an affinity exclusion operation (220), and extracting nucleic acids from the affinity reduced fraction (230).

Example 3

Nucleic Acid Extraction with Extraction Enhancement Operation and Affinity Exclusion Operation One variation of the invention is shown in FIG. 3, where the method comprises the steps of obtaining a biological sample (300), pre-processing the sample to obtain a fraction comprising a heterogeneous collection of nucleic acid-containing materials (310), performing an affinity exclusion operation (320), performing an extraction enhancement operation (330), and extracting nucleic acids.

Example 4

Nucleic Acid Extraction and Analysis from a Heterogeneous Collection of Nucleic Acid-Containing Materials Heterogeneous collections of nucleic acid-containing materials can be isolated from a biological sample from a subject that has or is suspected to have cancer. A urine sample is collected from the subject. In the pre-processing step, a fraction containing nucleic acid-containing materials is enriched by centrifugation or filtration from the urine. The resulting fraction contains a heterogeneous collection of nucleic acid-containing materials, which includes a mixture of microvesicles and cells in addition to other nucleic acid-containing materials. This fraction is then incubated with extraction enhancement agents, such as RNase inhibitors, to prevent or mitigate those factors that may prevent high quality nucleic acid extraction. Then, the fraction is subjected to an affinity enrichment operation to enrich for the potential circulating tumor cells and microvesicles of particular interest. A surface antigen carried by both the circulating tumor cells and microvesicles is used to select for and purify these particular nucleic acid-containing materials from the remaining mixture. Nucleic acids from the purified circulating tumor cells and microvesicles are extracted and analyzed for the presence, absence, or levels of genetic aberrations that are associated with the presence or absence of malignant cancer; or stage or grade of the tumor from which the cells and microvesicles may have originated from.

REFERENCES

Abravaya, K., J. J. Carrino, S. Muldoon, and H. H. Lee. 1995. Detection of point mutations with a modified ligase chain reaction (Gap-LCR). *Nucleic Acids Res.* 23:675-82.

Agarwal, B., O. J. Ludwig, B. T. Collins, and C. Cortese. 2008 Immunostaining as an adjunct to cytology for diagnosis of pancreatic adenocarcinoma. *Clin Gastroenterol Repatol.* 6:1425-31.

Agis, H., M. T. Krauth, A. Bohm, I. Mosberger, L. Mullauer, I. Simonitsch-Klupp, A. F. Walls, H. P. Horny, and P. Valent. 2006a. Identification of basogranulin (BB1) as a novel immunohistochemical marker of basophils in normal bone marrow and patients with myeloproliferative disorders. *Am J Clin Pathol.* 125:273-81.

Agis, H., M. T. Krauth, I. Mosberger, L. Mullauer, I. Simonitsch-Klupp, L. B. Schwartz, D. Printz, A. Bohm, G. Fritsch, H. P. Horny, and P. Valent. 2006b. Enumeration and immunohistochemical characterisation of bone marrow basophils in myeloproliferative disorders using the basophil specific monoclonal antibody 2D7. *J Clin Pathol.* 59:396-402.

Agre, P., B. L. Smith, and S. Hartel-Schenk. 1990. Biochemistry of the erythrocyte Rh polypeptides: a review. *Yule J Biol Med.* 63:461-7.

Al-Hajj, M., M. S. Wicha, A. Benito-Hernandez, S. J. Morrison, and M. F. Clarke. 2003. Prospective identification of tumorigenic breast cancer cells. *Proc Natl Acad Sci USA.* 100:3983-8.

Al-Nedawi, K., B. Meehan, J. Micallef, V. Lhotak, L. May, A. Guha, and J. Rak. 2008. Intercellular transfer of the oncogenic receptor EGFRvIII by microvesicles derived from tumour cells. *Nat Cell Biol.* 10:619-24.

Allard, W. J., J. Matera, M. C. Miller, M. Repollet, M. C. Connelly, C. Rao, A. G. Tibbe, J. W. Uhr, and L. W. Terstappen. 2004. Tumor cells circulate in the peripheral blood of all major carcinomas but not in healthy subjects or patients with nonmalignant diseases. *Clin Cancer Res.* 10:6897-904.

Alsayed, Y., H. Ngo, J. Runnels, X. Leleu, U. K. Singha, C. M. Pitsillides, J. A. Spencer, T. Kimlinger, J. M. Ghobrial, X. Jia, G. Lu, M. Timm, A. Kumar, D. Cote, I. Veilleux, K. E. Hedin, G. D. Roodman, T. E. Witzig, A. L. Kung, T. Hideshima, K. C. Anderson, C. P. Lin, and I. M. Ghobrial. 2007. Mechanisms of regulation of CXCR4/SDF-1 (CXCL12)-dependent migration and homing in multiple myeloma. *Blood.* 109:2708-17.

Alvero, A. B., R. Chen, H. H. Fu, M. Montagna, P. E. Schwartz, T. Rutherford, D. A. Silasi, K. D. Steffensen, M. Waldstrom, I. Visintin, and G. Mor. 2009. Molecular phenotyping of human ovarian cancer stem cells unravels the mechanisms for repair and chemoresistance. *Cell Cycle.* 8:158-66.

Ammons, W. S., R. J. Bauer, A. H. Horwitz, Z. J. Chen, E. Bautista, H. H. Ruan, M. Abramova, K. R. Scott, and R. L. Dedrick. 2003. In vitro and in vivo pharmacology and pharmacokinetics of a human engineered monoclonal antibody to epithelial cell adhesion molecule. *Neoplasia.* 5:146-54.

Andersson, L. C., C. G. Gahmberg, L. Teerenhovi, and P. Vuopio. 1979. Glycophorin A as a cell surface marker of early erythroid differentiation in acute leukemia. *MU Cancer.* 24:717-20.

Avent, N. D., W. Liu, K. M. Warner, W. J. Mawby, J. W. Jones, K. Ridgwell, and M. J. Tanner. 1996. Immunochemical analysis of the human erythrocyte Rh polypeptides. *J Biol Chem.* 271:14233-9.

Baig, J. A., J. M. Alam, S. R. Mahmood, M. Baig, R. Shaheen, I. Sultana, and A. Waheed. 2009. Hepatocellular carcinoma (HCC) and diagnostic significance of A-fetoprotein (AFP). *J Ayub Med Coll Abbottabad.* 21:72-5.

Ball, E. D. 1995. Introduction: workshop summary of the CD15 monoclonal antibody panel from the Fifth International Workshop on Leukocyte Antigens. *Eur J Morphol.* 33:95-100.

Balzar, M., M. J. Winter, C. J. de Boer, and S. V. Litvinov. 1999. The biology of the 17-1A antigen (Ep-CAM). *J Mol Med.* 77:699-712.

Bao, S., Q. Wu, Z. Li, S. Sathornsumetee, H. Wang, R. E. McLendon, A. B. Hjelmeland, and J. N. Rich. 2008. Targeting cancer stem cells through L1 CAM suppresses glioma growth. *Cancer Res.* 68:6043-8.

Bao, S., Q. Wu, R. E. McLendon, Y. Hao, Q. Shi, A. B. Hjelmeland, M. W. Dewhirst, D. D. Bigner, and J. N. Rich. 2006a. Glioma stem cells promote radioresistance by preferential activation of the DNA damage response. *Nature.* 444:756-60.

Bao, S., Q. Wu, S. Sathornsumetee, Y. Hao, Z. Li, A. B. Hjelmeland, Q. Shi, R. E. McLendon, D. D. Bigner, and J. N. Rich. 2006b. Stem cell-like glioma cells promote tumor angiogenesis through vascular endothelial growth factor. *Cancer Res.* 66:7843-8.

Bembridge, G. P., K. R. Parsons, P. Sopp, N. D. MacHugh, and C. J. Howard. 1993. Comparison of monoclonal antibodies with potential specificity for restricted isoforms of the leukocyte common antigen (CD45R). *Vet Immunol Immunopathol.* 39:129-36.

Berrington, J. E., D. Barge, A. C. Fenton, A. J. Cant, and G. P. Spickett. 2005. Lymphocyte subsets in term and significantly preterm UK infants in the first year of life analysed by single platform flow cytometry. *Clin Exp Immunol.* 140:289-92.

Boman, B. M., and E. Huang. 2008. Human colon cancer stem cells: a new paradigm in gastrointestinal oncology. *J Clin Oncol.* 26:2828-38.

Bonnet, D., and J. E. Dick. 1997. Human acute myeloid leukemia is organized as a hierarchy that originates from a primitive hematopoietic cell. *Nat Med.* 3:730-7.

Borgono, C. A., L. Grass, A. Soosaipillai, G. M. Yousef, C. D. Petraki, D. H. Howarth, S. Fracchioli, D. Katsaros, and E. P. Diamandis. 2003. Human kallikrein 14: a new potential biomarker for ovarian and breast cancer. *Cancer Res.* 63:9032-41.

Borregaard, N., M. Sehested, B. S. Nielsen, H. Sengelov, and L. Kjeldsen. 1995. Biosynthesis of granule proteins in normal human bone marrow cells. Gelatinase is a marker of terminal neutrophil differentiation. *Blood.* 85:812-7.

Bossi, A., F. Bonini, A. P. Turner, and S. A. Piletsky. 2007. Molecularly imprinted polymers for the recognition of proteins: the state of the art. *Biosens Bioelectron.* 22:1131-7.

Chan, K. S., I. Espinosa, M. Chao, D. Wong, L. Ailles, M. Diehn, H. Gill, J. Presti, Jr., H. Y. Chang, M. van de Rijn, L. Shortliffe, and I. L. Weissman. 2009. Identification, molecular characterization, clinical prognosis, and therapeutic targeting of human bladder tumor-initiating cells. *Proc Natl Acad Sci USA.* 106:14016-21.

Chang, K., and I. Pastan. 1996. Molecular cloning of mesothelin, a differentiation antigen present on mesothelium, mesotheliomas, and ovarian cancers. *Proc Natl Acad Sci USA.* 93:136-40.

Chang, S. S., V. E. Reuter, W. D. Heston, N. H. Bander, L. S. Grauer, and P. B. Gaudin. 1999. Five different anti-prostate-specific membrane antigen (PSMA) antibodies confirm PSMA expression in tumor-associated neovasculature. *Cancer Res.* 59:3192-8.

Chen, C., J. Skog, C. H. Hsu, R. T. Lessard, L. Balaj, T. Wurdinger, B. S. Carter, X. O. Breakefield, M. Toner, and D. Irimia. 2010. Microfluidic isolation and transcriptome analysis of serum microvesicles. *Lab Chip.* 10:505-11.

Chen, Y. C., G. Pohl, T. L. Wang, P. J. Morin, B. Risberg, G. B. Kristensen, A. Yu, B. Davidson, and M. Shih Ie. 2005. Apolipoprotein E is required for cell proliferation and survival in ovarian cancer. *Cancer Res.* 65:331-7.

Cheruvanky, A., H. Zhou, T. Pisitkun, J. B. Kopp, M. A. Knepper, P. S. Yuen, and R. A. Star. 2007. Rapid isolation of urinary exosomal biomarkers using a nanomembrane ultrafiltration concentrator. *Am J Physiol Renal Physiol.* 292:F1657-61.

Clement, L. T., A. B. Tilden, and N. E. Dunlap. 1985. Analysis of the monocyte Fc receptors and antibody-mediated cellular interactions required for the induction of T cell proliferation by anti-T3 antibodies. *J Immunol.* 135:165-71.

Coiffier, B. 2007. Rituximab therapy in malignant lymphoma. *Oncogene.* 26:3603-13. Collins, A. T., P. A. Berry, C. Hyde, M. J. Stower, and N. J. Maitland. 2005. Prospective identification of tumorigenic prostate cancer stem cells. *Cancer Res.* 65:10946-51.

Cotton, R. G., N. R. Rodrigues, and R. D. Campbell. 1988. Reactivity of cytosine and thymine in single-base-pair mismatches with hydroxylamine and osmium tetroxide and its application to the study of mutations. *Proc Natl Acad Sci USA.* 85:4397-401.

Cowell, J. K., and K. C. Lo. 2009. Application of oligonucleotides arrays for coincident comparative genomic hybridization, ploidy status and loss of heterozygosity studies in human cancers. *Methods Mol Biol.* 556:47-65.

Cox, C. V., R. S. Evely, A. Oakhill, D. H. Pamphilon, N. J. Goulden, and A. Blair. 2004. Characterization of acute lymphoblastic leukemia progenitor cells. *Blood.* 104:2919-25.

Dallas, N. A., L. Xia, F. Fan, M. J. Gray, P. Gaur, G. van Buren, 2nd, S. Samuel, M. P. Kim, S. J. Lim, and L. M. Ellis. 2009. Chemoresistant colorectal cancer cells, the cancer stem cell phenotype, and increased sensitivity to insulin-like growth factor-I receptor inhibition. *Cancer Res.* 69:1951-7.

De Clerck, L. S., C. M. De Gendt, C. H. Bridts, N. Van Osselaer, and W. J. Stevens. 1995. Expression of neutrophil activation markers and neutrophil adhesion to chondrocytes in rheumatoid arthritis patients: relationship with disease activity. *Res Immunol.* 146:81-7.

de la Fuente, M. A., V. Tovar, N. Villamor, N. Zapater, P. Pizcueta, E. Campo, J. Bosch, and P. Engel. 2001. Molecular characterization and expression of a novel human leukocyte cell-surface marker homologous to mouse Ly-9. *Blood.* 97:3513-20.

Dhanasekaran, S. M., T. R. Barrette, D. Ghosh, R. Shah, S. Varambally, K. Kurachi, K. J. Pienta, M. A. Rubin, and A. M. Chinnaiyan. 2001. Delineation of prognostic biomarkers in prostate cancer. *Nature.* 412:822-6.

Ding, Y., W. Jiang, Y. Su, H. Zhou, and Z. Zhang. 2004. Expression and purification of recombinant cytoplasmic domain of human erythrocyte band 3 with hex ahistidine tag or chitin-binding tag in *Escherichia coli. Protein Expr Purif.* 34:167-75.

Dirks, P. B. 2001. Glioma migration: clues from the biology of neural progenitor cells and embryonic CNS cell migration. *J Neurooncol.* 53:203-12.

Ducrest, S., F. Meier, C. Tschopp, R. Pavlovic, and C. A. Dahinden. 2005. Flowcytometric analysis of basophil counts in human blood and inaccuracy of hematology analyzers. *Allergy.* 60:1446-50.

Eramo, A., F. Lotti, G. Sette, E. Pilozzi, M. Biffoni, A. Di Virgilio, C. Conticello, L. Ruco, C. Peschle, and R. De Maria. 2008. Identification and expansion of the tumorigenic lung cancer stem cell population. *Cell Death Differ.* 15:504-14.

Falleni, M., C. Pellegrini, A. Marchetti, B. Oprandi, F. Buttitta, F. Barassi, L. Santambrogio, G. Coggi, and S. Bosari. 2003. Survivin gene expression in early-stage non-small cell lung cancer. *J Pathol.* 200:620-6.

Fayle, D. R., P. S. Sim, D. K. Irvine, and W. F. Doe. 1985. Isolation of plasma membrane from human blood monocytes. Subcellular fractionation and marker distribution. *Eur J Biochem.* 147:409-19.

Ferrandina, G., G. Bonanno, L. Pierelli, A. Perillo, A. Procoli, A. Mariotti, M. Corallo, E. Martinelli, S. Rutella, A. Paglia, G. Zannoni, S. Mancuso, and G. Scambia. 2008. Expression of CD 133-1 and CD 133-2 in ovarian cancer. *Int J Gynecol Cancer.* 18:506-14.

Figarella-Branger, D. F., P. L. Durbec, and G. N. Rougon. 1990. Differential spectrum of expression of neural cell adhesion molecule isoforms and L1 adhesion molecules on human neuroectodermal tumors. *Cancer Res.* 50:6364-70.

Fillmore, C. M., and C. Kuperwasser. 2008. Human breast cancer cell lines contain stem-like cells that self-renew, give rise to phenotypically diverse progeny and survive chemotherapy. *Breast Cancer Res.* 10:R25.

Fink, R., M. Al-Obaidi, S. Grewal, M. Winter, and J. Pepper. 2003. Monocyte activation markers during cardiopulmonary bypass. *Perfusion.* 18:83-6.

Fischer, S. G., and L. S. Lerman. 1979a. Length-independent separation of DNA restriction fragments in two-dimensional gel electrophoresis. *Cell.* 16:191-200.

Fischer, S. G., and L. S. Lerman. 1979b. Two-dimensional electrophoretic separation of restriction enzyme fragments of DNA. *Methods Enzymol.* 68:183-91.

Flaherty, S. F., D. T. Golenbock, F. H. Milham, and R. R. Ingalls. 1997. CD11/CD18 leukocyte integrins: new signaling receptors for bacterial endotoxin. *J Surg Res.* 73:85-9.

Flanagan, J., J. Middeldorp, and T. Sculley. 2003. Localization of the Epstein-Barr virus protein LMP 1 to exosomes. *J Gen Virol.* 84:1871-9.

Fong, M. Y., and S. S. Kakar. 2010. The role of cancer stem cells and the side population in epithelial ovarian cancer. *Histol Histopathol.* 25:113-20.

Galli, R., E. Binda, U. Orfanelli, B. Cipelletti, A. Gritti, S. De Vitis, R. Fiocco, C. Foroni, F. Dimeco, and A. Vescovi. 2004. Isolation and characterization of tumorigenic, stem-like neural precursors from human glioblastoma. *Cancer Res.* 64:7011-21.

Gallin, J. I., R. J. Jacobson, B. E. Seligmann, J. A. Metcalf, J. H. McKay, R. A. Sacher, and H. L. Malech. 1986. A neutrophil membrane marker reveals two groups of chronic myelogenous leukemia and its absence may be a marker of disease progression. *Blood.* 68:343-6.

Geiss, G. K., R. E. Bumgarner, B. Birditt, T. Dahl, N. Dowidar, D. L. Dunaway, H. P. Fell, S. Ferree, R. D. George, T. Grogan, J. J. James, M. Maysuria, J. D. Mitton, P. Oliveri, J. L. Osborn, T. Peng, A. L. Ratcliffe, P. J. Webster, E. H. Davidson, and L. Hood. 2008. Direct multiplexed measurement of gene expression with color-coded probe pairs. *Nat Biotechnol.* 26:317-25.

Ginestier, C., M. H. Hur, E. Charafe-Jauffret, F. Monville, J. Dutcher, M. Brown, J. Jacquemier, P. Viens, C. C. Kleer, S. Liu, A. Schott, D. Hayes, D. Birnbaum, M. S. Wicha, and G. Dontu. 2007. ALDH1 is a marker of normal and malignant human mammary stem cells and a predictor of poor clinical outcome. *Cell Stein Cell.* 1:555-67.

Goel, S., R. J. Bauer, K. Desai, A. Bulgaru, T. Iqbal, B. K. Strachan, G. Kim, A. Kaubisch, G. F. Vanhove, G. Goldberg, and S. Mani. 2007. Pharmacokinetic and safety study of subcutaneously administered weekly ING-1, a human engineered monoclonal antibody targeting human EpCAM, in patients with advanced solid tumors. *Ann Oncol.* 18:1704-7.

Guatelli, J. C., K. M. Whitfield, D. Y. Kwoh, K. J. Barringer, D. D. Richman, and T. R. Gingeras. 1990. Isothermal, in vitro amplification of nucleic acids by a multienzyme reaction modeled after retroviral replication. *Proc Natl Acad Sci USA.* 87:1874-8.

Gucrini, F. R., C. Agliardi, M. Zanzottera, S. Delbuc, E. Pagani, C. Tinelli, R. Boldorini, P. G. Car, C. Veggiani, and P. Ferrante. 2006. Human leukocyte antigen distribution analysis in North Italian brain Glioma patients: an association with HLA-DRB1*14. *J Neurooncol.* 77:213-7.

Gurlek, A., N. Karavitaki, O. Ansorge, and J. A. Wass. 2007. What are the markers of aggressiveness in prolactinomas? Changes in cell biology, extracellular matrix components, angiogenesis and genetics. *Eur J Endocrinol.* 156:143-53.

Hahn, P. J. 1993. Molecular biology of double-minute chromosomes. *Bioessays.* 15:477-84.

Hannigan, M., L. Zhan, Y. Ai, and C. K. Huang. 2001. Leukocyte-specific gene 1 protein (LSP1) is involved in chemokine KC-activated cytoskeletal reorganization in murine neutrophils in vitro. *J Leukoc Biol.* 69:497-504.

Heimberger, A. B., D. Suki, D. Yang, W. Shi, and K. Aldapc. 2005. The natural history of EGFR and EGFRvIII in glioblastoma patients. J Trans" Med. 3:38.

Hemmati, H. D., I. Nakano, J. A. Lazareff, M. Masterman-Smith, D. H. Geschwind, M. Bronner-Fraser, and H. T. Kornblum. 2003. Cancerous stem cells can arise from pediatric brain tumors. *Proc Natl Acad Sci USA.* 100:15178-83.

Hermann, P. C., S. L. Huber, T. Herrler, A. Aicher, J. W. Ellwart, M. Guba, C. J. Bruns, and C. Heeschen. 2007. Distinct populations of cancer stem cells determine tumor growth and metastatic activity in human pancreatic cancer. *Cell Stem Cell.* 1:313-23.

Hessels, D., F. P. Smit, G. W. Verhaegh, J. A. Witjes, E. B. Cornel, and J. A. Schalken. 2007. Detection of TMPRSS2-ERG fusion transcripts and prostate cancer antigen 3 in urinary sediments may improve diagnosis of prostate cancer. *Clin Cancer Res.* 13:5103-8.

Hill, C., S. B. Hunter, and D. J. Brat. 2003. Genetic markers in glioblastoma: prognostic significance and future therapeutic implications. *Adv Anat Pathol.* 10:212-7.

Hoffman, B. R., D. Katsaros, A. Scorilas, P. Diamandis, S. Fracchioli, I. A. Rigault de la Longrais, T. Colgan, M. Puopolo, G. Giardina, M. Massobrio, and E. P. Diamandis. 2002 Immunofluorometric quantitation and histochemical localisation of kallikrein 6 protein in ovarian cancer tissue: a new independent unfavourable prognostic biomarker. *Br J Cancer.* 87:763-71.

Hosen, N., C. Y. Park, N. Tatsumi, Y. Oji, H. Sugiyama, M. Gramatzki, A. M. Krensky, and I. L. Weissman. 2007. CD96 is a leukemic stem cell-specific marker in human acute myeloid leukemia. *Proc Natl Acad Sci USA.* 104:11008-13.

Hough, C. D., K. R. Cho, A. B. Zonderman, D. R. Schwartz, and P. J. Morin. 2001. Coordinately up-regulated genes in ovarian cancer. *Cancer Res.* 61:3869-76.

Hurt, E. M., B. T. Kawasaki, G. J. Klarmann, S. B. Thomas, and W. L. Farrar. 2008. CD44+ CD24(−) prostate cells are early cancer progenitor/stem cells that provide a model for patients with poor prognosis. *Br J Cancer.* 98:756-65.

Ignatova, T. N., V. G. Kukekov, E. D. Laywell, O. N. Suslov, F. D. Vrionis, and D. A. Steindler. 2002. Human cortical glial tumors contain neural stem-like cells expressing astroglial and neuronal markers in vitro. *Glia.* 39:193-206.

Ishikawa, F., S. Yoshida, Y. Saito, A. Hijikata, H. Kitamura, S. Tanaka, R. Nakamura, T. Tanaka, H. Tomiyama, N. Saito, M. Fukata, T. Miyamoto, B. Lyons, K. Ohshima, N. Uchida, S. Taniguchi, O. Ohara, K. Akashi, M. Harada, and L. D. Shultz. 2007. Chemotherapy-resistant human AML stem cells home to and engraft within the bonemarrow endosteal region. *Nat Biotechnol.* 25:1315-21.

Jackman, D. M., V. A. Miller, L. A. Cioffredi, B. Y. Yeap, P. A. Janne, G. J. Riely, M. G. Ruiz, G. Giaccone, L. V. Scquist, and B. E. Johnson. 2009 Impact of epidermal growth factor receptor and KRAS mutations on clinical outcomes in previously untreated non-small cell lung cancer patients: results of an online tumor registry of clinical trials. *Clin Cancer Res.* 15:5267-73.

Jiang, F., Q. Qiu, A. Khanna, N. W. Todd, J. Deepak, L. Xing, H. Wang, Z. Liu, Y. Su, S. A. Stass, and R. L. Katz. 2009. Aldehyde dehydrogenase 1 is a tumor stem cell-associated marker in lung cancer. *Mol Cancer Res.* 7:330-8.

Jiang, J., B. Kong, B. Shen, L. Li, X. Yang, H. Hou, Q. Shi, D. Ma, and X. Ma. 2005. High dose chemotherapy and transplantation of hematopoietic progenitors from murine D3 embryonic stem cells. *J Chemother.* 17:302-8.

Jin, L., J. J. Hemperly, and R. V. Lloyd. 1991. Expression of neural cell adhesion molecule in normal and neoplastic human neuroendocrine tissues. *Am J Pathol.* 138:961-9.

Jin, L., K. J. Hope, Q. Zhai, F. Smadja-Joffe, and J. E. Dick. 2006. Targeting of CD44 eradicates human acute myeloid leukemic stem cells. *Nat Med.* 12:1167-74.

Johnson, S., D. Evans, S. Laurenson, D. Paul, A. G. Davies, P. K. Ferrigno, and C. Walti. 2008. Surface-immobilized peptide aptamers as probe molecules for protein detection. *Anal Chem.* 80:978-83.

Jonas, L., C. Schutt, P. Neels, H. Walzel, and E. Siegl. 1990. Electron microscopic study of receptor mediated endocytosis of a monoclonal antibody (RoMo-1) against the surface marker CD 14 of human monocytes. *Acta Histochem Suppl.* 39:339-44.

Kalli, K. R., A. L. Oberg, G. L. Keeney, T. J. Christianson, P. S. Low, K. L. Knutson, and L. C. Hartmann 2008. Folate receptor alpha as a tumor target in epithelial ovarian cancer. *Gynecol Oncol.* 108:619-26.

Kan, Y. W., and A. M. Dozy. 1978a. Antenatal diagnosis of sickle-cell anaemia by D.N.A. analysis of amniotic-fluid cells. *Lancet.* 2:910-2.

Kan, Y. W., and A. M. Dozy. 1978b. Polymorphism of DNA sequence adjacent to human beta-globin structural gene: relationship to sickle mutation. *Proc Natl Acad Sci USA.* 75:5631-5.

Kansas, G. S., O. Spertini, L. M. Stoolman, and T. F. Tedder. 1991. Molecular mapping of functional domains of the leukocyte receptor for endothelium, LAM-1. *J Cell Biol.* 114:351-8.

Kasinrerk, W., E. Fiebiger, I. Stefanova, T. Baumruker, W. Knapp, and H. Stockinger. 1992. Human leukocyte activation antigen M6, a member of the 1 g superfamily, is the species homologue of rat OX-47, mouse basigin, and chicken HT7 molecule. *J Immunol.* 149:847-54.

Kawanishi, H., Y. Matsui, M. Ito, J. Watanabe, T. Takahashi, K. Nishizawa, H. Nishiyama, T. Kamoto, Y. Mikami, Y. Tanaka, G. Jung, H. Akiyama, H. Nobumasa, P. Guilford, A. Reeve, Y. Okuno, G. Tsujimoto, E. Nakamura, and O. Ogawa. 2008. Secreted CXCL1 is a potential mediator and marker of the tumor invasion of bladder cancer. *Clin Cancer Res.* 14:2579-87.

Keller, S., C. Rupp, A. Stoeck, S. Runz, M. Fogel, S. Lugert, H. D. Hager, M. S. Abdel-Bakky, P. Gutwein, and P. Altevogt. 2007. CD24 is a marker of exosomes secreted into urine and amniotic fluid. *Kidney Int.* 72:1095-102.

Kepley, C. L., S. S. Craig, and L. B. Schwartz. 1995. Identification and partial characterization of a unique marker for human basophils. *J Immunol.* 154:6548-55.

Kim, M., H. Turnquist, J. Jackson, M. Sgagias, Y. Yan, M. Gong, M. Dean, J. G. Sharp, and K. Cowan. 2002. The multidrug resistance transporter ABCG2 (breast cancer resistance protein 1) effluxes Hoechst 33342 and is overexpressed in hematopoietic stem cells. *Clin. Cancer Res.* 8:22-8.

Kobayashi, D., S. Aizawa, T. Maeda, I. Tsuboi, H. Yabuuchi, J. Nezu, A. Tsuji, and I. Tamai. 2004. Expression of organic cation transporter OCTN 1 in hematopoietic cells during erythroid differentiation. *Exp Hematol.* 32:1156-62.

Kojima, T., and T. Kitamura. 1999. A signal sequence trap based on a constitutively active cytokine receptor. *Nat Biotechnol.* 17:487-90.

Komminoth, P., J. Roth, P. M. Lackie, D. Bitter-Suermann, and P. U. Heitz. 1991. Polysialic acid of the neural cell adhesion molecule distinguishes small cell lung carcinoma from carcinoids. *Am J Pathol.* 139:297-304.

Korkaya, H., A. Paulson, F. Iovino, and M. S. Wicha. 2008. HER2 regulates the mammary stem/progenitor cell population driving tumorigenesis and invasion. *Oncogene.* 27:6120-30.

Kwoh, D. Y., G. R. Davis, K. M. Whitfield, H. L. Chappelle, L. J. DiMichele, and T. R. Gingeras. 1989. Transcription-based amplification system and detection of amplified human immunodeficiency virus type 1 with a bead-based sandwich hybridization format. *Proc Natl Acad Sci USA.* 86:1173-7.

Lai, R., L. Visser, and S. Poppema. 1991. Tissue distribution of restricted leukocyte common antigens. A comprehensive study with protein- and carbohydrate-specific CD45R antibodies. *Lab Invest.* 64:844-54.

Landegren, U., R. Kaiser, J. Sanders, and L. Hood. 1988. A ligase-mediated gene detection technique. *Science.* 241:1077-80.

Lapidot, T., C. Sirard, J. Vormoor, B. Murdoch, T. Hoang, J. Caceres-Cortes, M. Minden, B. Paterson, M. A. Caligiuri, and J. E. Dick. 1994. A cell initiating human acute myeloid leukaemia after transplantation into SCID mice. *Nature.* 367:645-8.

Laxman, B., D. S. Morris, J. Yu, J. Siddiqui, J. Cao, R. Mehra, R. J. Lonigro, A. Tsodikov, J. T. Wei, S. A. Tomlins, and A. M. Chinnaiyan. 2008. A first-generation multiplex biomarker analysis of urine for the early detection of prostate cancer. *Cancer Res.* 68:645-9.

Lee, J., S. Kotliarova, Y. Kotliarov, A. Li, Q. Su, N. M. Donin, S. Pastorino, B. W. Purow, N. Christopher, W. Zhang, J. K. Park, and H. A. Fine. 2006. Tumor stem cells derived from glioblastomas cultured in bFGF and EGF more closely mirror the phenotype and genotype of primary tumors than do serum-cultured cell lines. *Cancer Cell.* 9:391-403.

Lewis, C. D., S. P. Clark, G. Felsenfeld, and H. Gould. 1988. An erythrocyte-specific protein that binds to the poly(dG) region of the chicken beta-globin gene promoter. *Genes Dev.* 2:863-73.

Li, B., Y. W. Zheng, Y. Sano, and H. Taniguchi. 2011. Evidence for mesenchymal-epithelial transition associated with mouse hepatic stem cell differentiation. *PLoS One.* 6:e17092.

Li, C., D. G. Heidt, P. Dalerba, C. F. Burant, L. Zhang, V. Adsay, M. Wicha, M. F. Clarke, and D. M. Simeone. 2007. Identification of pancreatic cancer stem cells. *Cancer Res.* 67:1030-7.

Li, J., L. Wang, H. Mamon, M. H. Kulke, R. Berbeco, and G. M. Makrigiorgos. 2008. Replacing PCR with COLD-PCR enriches variant DNA sequences and redefines the sensitivity of genetic testing. *Nat Med.* 14:579-84.

Lim, S. C., and S. H. Oh. 2005. The role of CD24 in various human epithelial neoplasias. *Pathol Res Pract.* 201:479-86.

Liu, G., X. Yuan, Z. Zeng, P. Tunici, H. Ng, I. R. Abdulkadir, L. Lu, D. Irvin, K. L. Black, and J. S. Yu. 2006. Analysis of gene expression and chemoresistance of CD133+ cancer stem cells in glioblastoma. *Mol Cancer.* 5:67.

Lu, K. H., A. P. Patterson, L. Wang, R. T. Marquez, E. N. Atkinson, K. A. Baggerly, L. R. Ramoth, D. G. Rosen, J. Liu, I. Hellstrom, D. Smith, L. Hartmann, D. Fishman, A. Berchuck, R. Schmandt, R. Whitaker, D. M. Gershenson, G. B. Mills, and R. C. Bast, Jr. 2004. Selection of potential markers for epithelial ovarian cancer with gene expression arrays and recursive descent partition analysis. *Clin Cancer Res.* 10:3291-300.

Lunter, P. C., J. W. van Kilsdonk, H. van Beek, I. M. Cornelissen, M. Bergers, P. H. Willems, G. N. van Muijen, and G. W. Swart. 2005. Activated leukocyte cell adhesion molecule (ALCAM/CD166/MEMD), a novel actor in invasive growth, controls matrix metalloproteinase activity. *Cancer Res.* 65:8801-8.

Luo, L. Y., D. Katsaros, A. Scorilas, S. Fracchioli, R. Piccinno, I. A. Rigault de la Longrais, D. J. Howarth, and E. P. Diamandis. 2001. Prognostic value of human kallikrein 10 expression in epithelial ovarian carcinoma. *Clin Cancer Res.* 7:2372-9.

Magklara, A., A. Scorilas, W. J. Catalona, and E. P. Diamandis. 1999. The combination of human glandular kallikrein and free prostate-specific antigen (PSA) enhances discrimination between prostate cancer and benign prostatic hyperplasia in patients with moderately increased total PSA. *Clin Chem.* 45:1960-6.

Magro, G., D. Perissinotto, M. Schiappacassi, S. Goletz, A. Otto, E. C. Muller, M. Bisceglia, G. Brown, T. Ellis, S. Grasso, A. Colombatti, and R. Penis. 2003. Proteomic and postproteomic characterization of keratan sulfate-glycanated isoforms of thyroglobulin and transferrin uniquely elaborated by papillary thyroid carcinomas. *Am J Pathol.* 163:183-96.

Marafioti, T., C. Mancini, S. Ascani, E. Sabattini, P. L. Zinzani, M. Pozzobon, K. Pulford, B. Falini, E. S. Jaffe, H. K. Muller-Hermelink, D. Y. Mason, and S. A. Pileri. 2004. Leukocyte-specific phosphoprotein-1 and PU.1: two useful markers for distinguishing T-cell-rich B-cell lymphoma from lymphocyte-predominant Hodgkin's disease. *Haematologica.* 89:957-64.

Masuoka, K., T. Toyosaki, Y. Tohya, J. Norimine, C. Kai, and T. Mikami. 1992. Monoclonal antibodies to feline lymphocyte membranes recognize the leukocyte-common antigen (CD45R). *J Vet Med Sci.* 54:865-70.

Matsui, T., K. Ohsumi, N. Ozawa, K. Shimada, S Sumitomo, K. Shimane, M. Kawakami, H. Nakayama, S. Sugii, Y. Ozawa, and S. Tohma. 2006. CD64 on neutrophils is a sensitive and specific marker for detection of infection in patients with rheumatoid arthritis. *J Rheumatol.* 33:2416-24.

Matsui, W., C. A. Huff, Q. Wang, M. T. Malehorn, J. Barber, Y. Tanhehco, B. D. Smith, C. I. Civin, and R. J. Jones. 2004. Characterization of clonogenic multiple myeloma cells. *Blood.* 103:2332-6.

Matthews, J. B., G. I. Mason, and R. M. Browne. 1988. Epithelial cell markers and proliferating cells in odontogenic jaw cysts. *J Pathol.* 156:283-90.

Mattick, J. S. 2004. RNA regulation: a new genetics? *Nat Rev Genet.* 5:316-23.

McGuckin, M. A., M. D. Walsh, B. G. Hohn, B. G. Ward, and R. G. Wright. 1995. Prognostic significance of MUC1 epithelial mucin expression in breast cancer. *Hum Pathol.* 26:432-9.

Miele, E. A., D. R. Mills, and F. R. Kramer. 1983. Autocatalytic replication of a recombinant RNA. *J Mol Biol.* 171:281-95.

Min-Oo, G., A. Fortin, M. F. Tam, P. Gros, and M. M. Stevenson. 2004. Phenotypic expression of pyruvate kinase deficiency and protection against malaria in a mouse model. *Genes Immun.* 5:168-75.

Monzani, E., F. Facchetti, E. Galmozzi, E. Corsini, A. Benetti, C. Cavazzin, A. Gritti, A. Piccinini, D. Porro, M. Santinami, G. Invernici, E. Parati, G. Alessandri, and C. A. La Porta. 2007. Melanoma contains CD133 and ABCG2 positive cells with enhanced tumourigenic potential. *Eur J Cancer.* 43:935-46.

Myers, R. M., Z. Larin, and T. Maniatis. 1985. Detection of single base substitutions by ribonuclease cleavage at mismatches in RNA:DNA duplexes. *Science.* 230:1242-6.

Nakazawa, H., D. English, P. L. Randell, K. Nakazawa, N. Martel, B. K. Armstrong, and H. Yamasaki. 1994. UV and skin cancer: specific p53 gene mutation in normal skin as a biologically relevant exposure measurement. *Proc Natl Acad Sci USA.* 91:360-4.

Naundorf, S., S. Preithner, P. Mayer, S. Lippold, A. Wolf, F. Hanakam, I. Fichtner, P. Kufer, T. Raum, G. Riethmuller, P. A. Baeuerle, and T. Dreier. 2002. In vitro and in vivo activity of MT201, a fully human monoclonal antibody for pancarcinoma treatment. *Int J Cancer.* 100:101-10.

Neve, R. M., K. Chin, J. Fridlyand, J. Yeh, F. L. Baehner, T. Fevr, L. Clark, N. Bayani, J. P. Coppe, F. Tong, T. Speed, P. T. Spellman, S. DeVries, A. Lapuk, N. J. Wang, W. L. Kuo, J. L. Stilwell, D. Pinkel, D. G. Albertson, F. M. Waldman, F. McCormick, R. B. Dickson, M. D. Johnson, M. Lippman, S. Ethicr, A. Gazdar, and J. W. Gray. 2006. A collection of breast cancer cell lines for the study of functionally distinct cancer subtypes. *Cancer Cell.* 10:515-27.

Nilsson, J., J. Skog, A. Nordstrand, V. Baranov, L. Mincheva-Nilsson, X. O. Breakefield, and A. Widmark. 2009. Prostate cancer-derived urine exosomes: a novel approach to biomarkers for prostate cancer. *Br J Cancer.* 100:1603-7.

Nishitani, Y., M. Iwano, Y. Yamaguchi, K. Harada, K. Nakatani, Y. Akai, T. Nishino, H. Shiiki, M. Kanauchi, Y. Saito, and E. G. Neilson. 2005. Fibroblast-specific protein 1 is a specific prognostic marker for renal survival in patients with IgAN. *Kidney Int.* 68:1078-85.

Niv, Y. 2008. MUC1 and colorectal cancer pathophysiology considerations. *World J Gastroenterol.* 14:2139-41.

O'Brien, C. A., A. Pollett, S. Gallinger, and J. E. Dick. 2007. A human colon cancer cell capable of initiating tumour growth in immunodeficient mice. *Nature.* 445:106-10.

Oberneder, R., D. Weckermann, B. Ebner, C. Quadt, P. Kirchinger, T. Raum, M. Locher, N. Prang, P. A. Baeuerle, and E. Leo. 2006. A phase I study with adecatumumab, a human antibody directed against epithelial cell adhesion molecule, in hormone refractory prostate cancer patients. *Eur J Cancer.* 42:2530-8.

Oldenborg, P. A., A. Zheleznyak, Y. F. Fang, C. F. Lagenaur, H. D. Gresham, and F. P. Lindberg. 2000. Role of CD47 as a marker of self on red blood cells. *Science.* 288:2051-4.

Orita, M., H. Iwahana, H. Kanazawa, K. Hayashi, and T. Sekiya. 1989. Detection of polymorphisms of human DNA by gel electrophoresis as single-strand conformation polymorphisms. *Proc Natl Acad Sci USA.* 86:2766-70.

Orozco, A. F., and D. E. Lewis. 2010. Flow cytometric analysis of circulating microparticles in plasma. *Cytometty A.* 77:502-14.

Ottaiano, A., A. di Palma, M. Napolitano, C. Pisano, S. Pignata, F. Tatangelo, G. Botti, A. M. Acquaviva, G. Castello, P. A. Ascicrto, R. V. Iaffaioli, and S. Scala. 2005 Inhibitory effects of anti-CXCR4 antibodies on human colon cancer cells. *Cancer Immunol Immunother.* 54:781-91.

Partin, A. W., W. J. Catalona, J. A. Finlay, C. Darte, D. J. Tindall, C. V. Young, G. G. Klee, D. W. Chan, H. G. Rittenhouse, R. L. Wolfert, and D. L. Woodrum. 1999. Use of human glandular kallikrein 2 for the detection of prostate cancer: preliminary analysis. *Urology.* 54:839-45.

Pelloski, C. E., K. V. Ballman, A. F. Furth, L. Zhang, E. Lin, E. P. Sulman, K. Bhat, J. M. McDonald, W. K. Yung, H. Colman, S. Y. Woo, A. B. Heimberger, D. Suki, M. D. Prados, S. M. Chang, F. G. Barker, 2nd, J. C. Buckner, C. D. James, and K. Aldape. 2007. Epidermal growth factor receptor variant III status defines clinically distinct subtypes of glioblastoma. *J Clin Oncol.* 25:2288-94.

Prince, M. E., R. Sivanandan, A. Kaczorowski, G. T. Wolf, M. J. Kaplan, P. Dalerba, I. L. Weissman, M. F. Clarke, and L. E. Ailles. 2007. Identification of a subpopulation of cells with cancer stem cell properties in head and neck squamous cell carcinoma. *Proc Natl Acad Sci USA.* 104:973-8.

Prinetti, A., M. Aureli, G. Illuzzi, S. Prioni, V. Nocco, F. Scandroglio, N. Gagliano, G. Tredici, V. Rodriguez-Menendez, V. Chigorno, and S. Sonnino. 2010. GM3 synthase overexpression results in reduced cell motility and in caveolin-1 upregulation in human ovarian carcinoma cells. *Glycobiology.* 20:62-77.

Punnoose, E. A., S. K. Atwal, J. M. Spoerke, H. Savage, A. Pandita, R. F. Yeh, A. Pirzkall, B. M. Fine, L. C. Amler, D. S. Chen, and M. R. Lackner. 2010. Molecular biomarker analyses using circulating tumor cells. *PLoS One.* 5:c12517.

Rangel, L. B., R. Agarwal, T. D'Souza, E. S. Pizer, P. L. Alo, W. D. Lancaster, L. Gregoire, D. R. Schwartz, K. R. Cho, and P. J. Morin. 2003. Tight junction proteins claudin-3 and claudin-4 are frequently overexpressed in ovarian cancer but not in ovarian cystadenomas. *Clin Cancer Res.* 9:2567-75.

Raposo, G., H. W. Nijman, W. Stoorvogel, R. Liejendekker, C. V. Harding, C. J. Melief, and H. J. Geuze. 1996. B lymphocytes secrete antigen-presenting vesicles. *J Exp Med.* 183:1161-72.

Ricci-Vitiani, L., D. C. Lombardi, E. Pilozzi, M. Biffoni, M. Todaro, C. Peschle, and R. De Maria. 2007. Identification and expansion of human colon-cancer-initiating cells. *Nature*. 445:111-5.

Rittenhouse, H. G., J. A. Finlay, S. D. Mikolajczyk, and A. W. Partin. 1998. Human Kallikrein 2 (hK2) and prostate-specific antigen (PSA): two closely related, but distinct, kallikreins in the prostate. *Crit Rev Clin Lab Sci*. 35:275-368.

Rosen, D. G., L. Wang, J. N. Atkinson, Y. Yu, K. H. Lu, E. P. Diamandis, I. Hellstrom, S. C. Mok, J. Liu, and R. C. Bast, Jr. 2005. Potential markers that complement expression of CA125 in epithelial ovarian cancer. *Gynecol Oncol*. 99:267-77.

Ross, J. S., C. E. Sheehan, H. A. Fisher, R. P. Kaufman, Jr., P. Kaur, K. Gray, I. Webb, G. S. Gray, R. Mosher, and B. V. Kallakury. 2003. Correlation of primary tumor prostatespecific membrane antigen expression with disease recurrence in prostate cancer. *Clin Cancer Res*. 9:6357-62.

Rudolph, P., B. Schubert, H. H. Wacker, R. Parwaresch, and C. Schubert. 1997. Immunophenotyping of dermal spindle cell tumors: diagnostic value of monocyte marker Ki-Mlp and histogenetic considerations. *Am J Surg Pathol*. 21:791-800.

Ruppert, J., D. Friedrichs, H. Xu, and J. H. Peters. 1991. IL-4 decreases the expression of the monocyte differentiation marker CD14, paralleled by an increasing accessory potency. *Immunobiology*. 182:449-64.

Sagiv, E., L. Memeo, A. Karin, D. Kazanov, J. Jacob-Hirsch, M. Mansukhani, G. Rechavi, H. Hibshoosh, and N. Arber. 2006. CD24 is a new oncogene, early at the multistep process of colorectal cancer carcinogenesis. *Gastroenterology*. 131:630-9.

Sainte-Laudy, J., and P. Belon. 2006. Improvement of flow cytometric analysis of basophil activation inhibition by high histamine dilutions. A novel basophil specific marker: CD 203c. *Homeopathy*. 95:3-8.

Salmaggi, A., A. Boiardi, M. Gelati, A. Russo, C. Calatozzolo, E. Ciusani, F. L. Sciacca, A. Ottolina, E. A. Parati, C. La Porta, G. Alessandri, C. Man-as, D. Croci, and M. De Rossi. 2006. Glioblastoma-derived tumorospheres identify a population of tumor stem-like cells with angiogenic potential and enhanced multidrug resistance phenotype. *Glia*. 54:850-60.

Santin, A. D., S. Bellone, J. J. Roman, J. K. McKenney, and S. Pecorelli. 2008. Trastuzumab treatment in patients with advanced or recurrent endometrial carcinoma overexpressing HER2/neu. *Int J Gynaecol Obstet*. 102:128-31.

Schatton, T., G. F. Murphy, N. Y. Frank, K. Yamaura, A. M. Waaga-Gasser, M. Gasser, Q. Zhan, S. Jordan, L. M. Duncan, C. Weishaupt, R. C. Fuhlbrigge, T. S. Kupper, M. H. Sayegh, and M. H. Frank. 2008. Identification of cells initiating human melanomas. *Nature*. 451:345-9.

Shan, B., T. Sugiura, and U. Yamashita. 1998. Five monoclonal antibodies against glycophorin A of human erythrocyte recognize glycoprotein of bovine erythrocyte. *Hybridoma*. 17:55-62.

Shangguan, D., Z. Cao, L. Meng, P. Mallikaratchy, K. Sefah, H. Wang, Y. Li, and W. Tan. 2008. Cell-specific aptamer probes for membrane protein elucidation in cancer cells. *J Proteome Res*. 7:2133-9.

Sheu, J. J., and M. Shih Ie. 2007. Clinical and biological significance of HLA-G expression in ovarian cancer. *Semin Cancer Biol*. 17:436-43.

Shih Ie, M., and B. Davidson. 2009. Pathogenesis of ovarian cancer: clues from selected overexpressed genes. *Future Oncol*. 5:1641-57.

Shmelkov, S. V., J. M. Butler, A. T. Hooper, A. Hormigo, J. Kushner, T. Milde, R. St Clair, M. Baljevic, I. White, D. K. Jin, A. Chadburn, A. J. Murphy, D. M. Valenzuela, N. W. Gale, G. Thurston, G. D. Yancopoulos, M. D'Angelica, N. Kemeny, D. Lyden, and S. Rafii. 2008. CD133 expression is not restricted to stem cells, and both CD133+ and CD133-metastatic colon cancer cells initiate tumors. *J Clin Invest*. 118:2111-20.

Siegel, N., A. Valli, C. Fuchs, M. Rosner, and M. Hengstschlager. 2009. Induction of mesenchymal/epithelial marker expression in human amniotic fluid stem cells. *Reprod Biomed Online*. 19:838-46.

Singh, S. K., I. D. Clarke, M. Terasaki, V. E. Bonn, C. Hawkins, J. Squire, and P. B. Dirks. 2003. Identification of a cancer stem cell in human brain tumors. *Cancer Res*. 63:5821-8.

Singh, S. K., C. Hawkins, I D Clarke, J. A. Squire, J. Bayani, T. Hide, R. M. Henkelman, M. D. Cusimano, and P. B. Dirks. 2004. Identification of human brain tumour initiating cells. *Nature*. 432:396-401.

Skog, J., T. Wurdinger, S. van Rijn, D. H. Meijer, L. Gainche, M. Sena-Esteves, W. T. Curry, Jr., B. S. Carter, A. M. Krichevsky, and X. O. Breakefield. 2008. Glioblastoma microvesicles transport RNA and proteins that promote tumour growth and provide diagnostic biomarkers. *Nat Cell Biol*. 10:1470-6.

Smith, L. M., A. Nesterova, M. C. Ryan, S. Duniho, M. Jonas, M. Anderson, R. F. Zabinski, M. K. Sutherland, H. P. Gerber, K. L. Van Orden, P. A. Moore, S. M. Ruben, and P. J. Carter. 2008. CD133/prominin-1 is a potential therapeutic target for antibody-drug conjugates in hepatocellular and gastric cancers. *Br J Cancer*. 99:100-9.

Spiekermann, K., J. Roesler, J. Elsner, M. L. Lohmann-Matthes, K. Welte, H. Malech, J. I. Gallin, and A. Emmendoerffer. 1996. Identification of the antigen recognized by the monoclonal antibody 31D8. *Exp Hematol*. 24:453-8.

Steemers, F. J., W. Chang, G. Lee, D. L. Barker, R. Shen, and K. L. Gunderson. 2006. Wholegenome genotyping with the single-base extension assay. *Nat Methods*. 3:31-3.

Stott, S. L., C. H. Hsu, D. I. Tsukrov, M. Yu, D. T. Miyamoto, B. A. Waltman, S. M. Rothenberg, A. M. Shah, M. E. Smas, G. K. Korir, F. P. Floyd, Jr., A. J. Gilman, J. B. Lord, D. Winokur, S. Springer, D. Irimia, S. Nagrath, L. V. Sequist, R. J. Lee, K. J. Isselbacher, S. Maheswaran, D. A. Haber, and M. Toner. 2010. Isolation of circulating tumor cells using a microvortex-generating herringbone-chip. *Prot Natl Acad Sci USA*. 107:18392-7.

Strojnik, T., G. V. Rosland, P. O. Sakariassen, R. Kavalar, and T. Lah. 2007. Neural stem cell markers, nestin and musashi proteins, in the progression of human glioma: correlation of nestin with prognosis of patient survival. *Surg Neural*. 68:133-43; discussion 143-4.

Strutz, F., H. Okada, C. W. Lo, T. Danoff, R. L. Carone, J. E. Tomaszewski, and E. G. Neilson. 1995. Identification and characterization of a fibroblast marker: FSP 1. *J Cell Biol*. 130:393-405.

Sun, Y. X., A. Schneider, Y. Jung, J. Wang, J. Dai, K. Cook, N. I. Osman, A. J. Koh-Paige, H. Shim, K. J. Pienta, E. T. Keller, L. K. McCauley, and R. S. Taichman. 2005. Skeletal localization and neutralization of the SDF-1 (CXCL12)/CXCR4 axis blocks prostate cancer metastasis and growth in osseous sites in vivo. *J Bone Miner Res*. 20:318-29.

Tao, D., Y. Shen, X. Feng, and H. Chen. 2000. The application of CD71 and Hoechst33258 to staining method for sorting fetal nucleated red blood cells in the peripheral blood of pregnant women. *Zhonghua Yi Xue Yi Chuan Xue Za Zhi.* 17:352-4.

Taylor-Papadimitriou, J., J. Burchell, D. W. Miles, and M. Dalziel. 1999. MUC1 and cancer. *Biochim Biophys Acta.* 1455:301-13.

Taylor, D. D., and C. Gercel-Taylor. 2008. MicroRNA signatures of tumor-derived exosomes as diagnostic biomarkers of ovarian cancer. *Gynecol Oncol.* 110:13-21.

Taylor, M. D., H. Poppleton, C. Fuller, X. Su, Y. Liu, P. Jensen, S. Magdaleno, J. Dalton, C. Calabrese, J. Board, T. Macdonald, J. Rutka, A. Guha, A. Gajjar, T. Curran, and R. J. Gilbertson. 2005. Radial glia cells are candidate stem cells of ependymoma. *Cancer Cell.* 8:323-35.

Telen, M. J., and J. A. Chasis. 1990. Relationship of the human erythrocyte Wrb antigen to an interaction between glycophorin A and band 3. *Blood.* 76:842-8.

Thibert, V., S. Bellucci, M. Cristofari, E. Gluckman, and C. Legrand. 1995. Increased platelet CD36 constitutes a common marker in myeloproliferative disorders. *Br J Haematol.* 91:618-24.

Thomas, S. N., Z. Tong, K. J. Stebe, and K. Konstantopoulos. 2009. Identification, characterization and utilization of tumor cell selectin ligands in the design of colon cancer diagnostics. *Biorheology.* 46:207-25.

Ting, D. T., D. Lipson, S. Paul, B. W. Brannigan, S. Akhavanfard, E. J. Coffman, G. Contino, V. Deshpande, A. J. Iafrate, S. Letovsky, M. N. Rivera, N. Bardeesy, S. Maheswaran, and D. A. Haber. 2011. Aberrant overexpression of satellite repeats in pancreatic and other epithelial cancers. *Science.* 331:593-6.

Todaro, M., M. P. Alea, A. B. Di Stefano, P. Cammareri, L. Vermeulen, F. Iovino, C. Tripodo, A. Russo, G. Gulotta, J. P. Medema, and G. Stassi. 2007. Colon cancer stem cells dictate tumor growth and resist cell death by production of interleukin-4. *Cell Stem Cell.* 1:389-402.

Tu, L., J. C. Poe, T. Kadono, G. M. Venturi, D. C. Bullard, T. F. Tedder, and D. A. Steeber. 2002. A functional role for circulating mouse L-selectin in regulating leukocyte/endothelial cell interactions in vivo. *J Immunol.* 169:2034-43.

Uchida, N., D. W. Buck, D. He, M. J. Reitsma, M. Masek, T. V. Phan, A. S. Tsukamoto, F. H. Gage, and I. L. Weissman. 2000. Direct isolation of human central nervous system stem cells. *Proc Natl Acad Sci USA.* 97:14720-5.

Valent, P., O. Majdic, D. Maurer, M. Bodger, M. Muhm, and P. Bettelheim. 1990. Further characterization of surface membrane structures expressed on human basophils and mast cells. *Int Arch Allergy Appi Iminunol.* 91:198-203.

Velculescu, V. E., L. Zhang, B. Vogelstein, and K. W. Kinzler. 1995. Serial analysis of gene expression. *Science.* 270:484-7.

Venturi, G. M., L. Tu, T. Kadono, A. 1. Khan, Y. Fujimoto, P. Oshel, C. B. Bock, A. S. Miller, R. M. Albrecht, P. Kubes, D. A. Steeber, and T. F. Tedder. 2003. Leukocyte migration is regulated by L-selectin endoproteolytic release. *Immunity.* 19:713-24.

Visintin, I., Z. Feng, G. Longton, D. C. Ward, A. B. Alvero, Y. Lai, J. Tenthorey, A. Leiser, R. Flores-Saaib, H. Yu, M. Azori, T. Rutherford, P. E. Schwartz, and G. Mor. 2008. Diagnostic markers for early detection of ovarian cancer. *Clin Cancer Res.* 14:1065-72.

Walker, F., L. Abramowitz, D. Benabderrahmane, X. Duval, V. Descatoire, D. Henin, T. Lehy, and T. Aparicio. 2009. Growth factor receptor expression in anal squamous lesions: modifications associated with oncogenic human papillomavirus and human immunodeficiency virus. *Hum Pathol.* 40:1517-27.

Went, P. T., A. Lugli, S. Meier, M. Bundi, M. Mirlacher, G. Sauter, and S. Dirnhofer. 2004. Frequent EpCam protein expression in human carcinomas. *Hum Pathol.* 35:122-8.

Yang, Y. M., and J. W. Chang. 2008. Bladder cancer initiating cells (BCICs) are among EMACD44v6+ subset: novel methods for isolating undetermined cancer stem (initiating) cells. *Cancer Invest.* 26:725-33.

Yang, Z. F., D. W. Ho, M. N. Ng, C. K. Lau, W. C. Yu, P. Ngai, P. W. Chu, C. T. Lam, R. T. Poon, and S. T. Fan. 2008. Significance of CD90+ cancer stem cells in human liver cancer. *Cancer Cell.* 13:153-66.

Yin, B. W., A. Dnistrian, and K. O. Lloyd. 2002. Ovarian cancer antigen CA125 is encoded by the MUC16 mucin gene. *Int J Cancer.* 98:737-40.

Yin, B. W., and K. O. Lloyd. 2001. Molecular cloning of the CA125 ovarian cancer antigen: identification as a new mucin, MUC16. *J Biol Chem.* 276:27371-5.

Yokohama, A., N. Tsukamoto, N. Hatsumi, M. Suto, T. Akiba, H. Uchiumi, T. Maehara, T. Matsushima, M. Karasawa, H. Murakami, S. Shinonome, H. Saito, and Y. Nojima. 2002. Acute basophilic leukemia lacking basophil-specific antigens: the importance of cytokine receptor expression in differential diagnosis. *Int J Hematol.* 75:309-13.

Young, D. 2007. Patent WO2007098571. Arius Research Inc.

Yousef, G. M., M. E. Polymeris, L. Grass, A. Soosaipillai, P. C. Chan, A. Scorilas, C. Borgono, N. Harbeck, B. Schmalfeldt, J. Dorn, M. Schmitt, and E. P. Diamandis. 2003a. Human kallikrein 5: a potential novel serum biomarker for breast and ovarian cancer. *Cancer Res.* 63:3958-65.

Yousef, G. M., M. E. Polymeris, G. M. Yacoub, A. Scorilas, A. Soosaipillai, C. Popalis, S. Fracchioli, D. Katsaros, and E. P. Diamandis. 2003b. Parallel overexpression of seven kallikrein genes in ovarian cancer. *Cancer Res.* 63:2223-7.

Yuan, X., J. Curtin, Y. Xiong, G. Liu, S. Waschsmann-Hogiu, D. L. Farkas, K. L. Black, and J. S. Yu. 2004. Isolation of cancer stem cells from adult glioblastoma multiforme. *Oncogene.* 23:9392-400.

Zeppernick, F., R. Ahmadi, B. Campos, C. Dictus, B. M. Helmke, N. Becker, P. Lichter, A. Unterberg, B. Radlwimmer, and C. C. Herold-Mende. 2008. Stem cell marker CD133 affects clinical outcome in glioma patients. *Clin Cancer Res.* 14:123-9.

Zhong, W. D., Y. X. Liang, S. X. Lin, L. Li, H. C. He, X. C. Bi, Z. D. Han, Q. S. Dai, Y. K. Ye, Q. B. Chen, Y. S. Wang, G. H. Zeng, G. Zhu, Z. Zhang, Z. N. Chen, and C. L. Wu. 2011. Expression of CD 147 is associated with prostate cancer progression. *Int J Cancer.*

Zwicker, J. I., H. A. Liebman, D. Neuberg, R. Lacroix, K. A. Bauer, B. C. Furie, and B. Furie. 2009. Tumor-derived tissue factor-bearing microparticles are associated with venous thromboembolic events in malignancy. *Clin Cancer Res.* 15:6830-40.

What is claimed is:

1. A method of extracting nucleic acid from a human biological sample, wherein the human biological sample comprises a heterogeneous collection of microvesicles, the method comprising the steps of:

a) filtering or centrifuging the biological sample to obtain a fraction comprising the heterogeneous collection of microvesicles, wherein the filtration or centrifugation excludes lipids, debris from dead cells, contaminants and PCR inhibitors;

b) depleting the fraction of at least 50% of microvesicles derived from erythrocytes by contacting the fraction with an affinity agent that binds to at least one surface marker to remove microvesicles that comprise the at least one surface marker from the fraction, wherein the surface marker is glycophorin A (CD235);

c) contacting the fraction from step (b) with at least one RNase inhibitor at least one reducing agent, at least one decoy substrate, at least one soluble receptor, at least one small interfering RNA, at least one RNA binding molecule, at least one RNase denaturing substance, or any combination thereof;

d) performing a processing step on the fraction from step (c), comprising washing the microvesicles, removing any RNases by size separation, denaturing any proteins, or a combination thereof;

e) extracting nucleic acid from the fraction from step (d).

2. The method of claim 1, further comprising contacting the fraction with an affinity agent that binds to at least one second surface marker selected from the markers listed in Table 1 or Table 2 to enrich and purify nucleic acid-containing materials that comprise the at least one second surface marker.

3. The method of claim 2, wherein the at least one second surface marker is selected from P-selectin, CD45, L1 cam, CD44, CD184, PDGFR, RH, CD3, CD19, CD20, CD56, CD11, CD14, CD90, CD326, or CD324.

4. The method of claim 3, wherein the at least one second surface marker is selected from L1cam, CD45, CD3, CD44 or CD184.

5. The method of claim 1, wherein the human biological sample is a bodily fluid.

6. The method of claim 5, wherein the bodily fluid is urine.

7. The method of claim 5, wherein the bodily fluid is serum or plasma.

8. The method of claim 1, wherein the RNase inhibitor is a protease.

9. The method of claim 1, wherein the nucleic acid obtained from practice of the extraction method is analyzed for the presence or absence of a genetic aberration associated with a disease or medical condition.

10. The method of claim 1, wherein the decoy substrate comprises synthetic RNA; or wherein the RNA binding molecule comprises an anti-RNA antibody, chaperone protein, or an RNase inhibitory protein; or wherein the RNase denaturing substance comprises a high osmolarity solution or detergent.

11. The method of claim 1, wherein the affinity agent comprises an antibody, an aptamer, an aptamer analog or a molecularly imprinted polymer specific for the marker.

12. The method of claim 1, wherein steps b and c occur sequentially.

13. The method of claim 1, wherein steps b and c occur concurrently.

14. The method of claim 1, wherein steps c and d occur sequentially.

15. The method of claim 1, wherein steps c and d occur concurrently.

* * * * *